(12) United States Patent
Bickert et al.

(10) Patent No.: US 10,007,102 B2
(45) Date of Patent: Jun. 26, 2018

(54) MICROSCOPE WITH SLIDE CLAMPING ASSEMBLY

(71) Applicant: SAKURA FINETEK U.S.A., INC., Torrance, CA (US)

(72) Inventors: Stefan Bickert, Ueberlingen (DE); Catherine Marie M. Wolf, Steinbrunn le Haut (FR)

(73) Assignee: Sakura Finetek U.S.A., Inc., Torrance, CA (US)

( * ) Notice: Subject to any disclaimer, the term of this patent is extended or adjusted under 35 U.S.C. 154(b) by 646 days.

(21) Appl. No.: 14/138,740

(22) Filed: Dec. 23, 2013

(65) Prior Publication Data

US 2015/0177504 A1   Jun. 25, 2015

(51) Int. Cl.
*G02B 21/34* (2006.01)
*G02B 21/26* (2006.01)
*G02B 21/00* (2006.01)

(52) U.S. Cl.
CPC ........... *G02B 21/34* (2013.01); *G02B 21/008* (2013.01); *G02B 21/26* (2013.01); *Y10T 29/49826* (2015.01)

(58) Field of Classification Search
CPC ....................................................... G02B 21/34
USPC .................................................. 359/391–398
See application file for complete search history.

(56) References Cited

U.S. PATENT DOCUMENTS

| | | | |
|---|---|---|---|
| 3,309,262 A | 3/1967 | Copeland et al. | |
| 3,525,803 A | 8/1970 | Smart | |
| 3,762,798 A * | 10/1973 | Grubb | G02B 21/26 359/394 |
| 3,765,851 A | 10/1973 | White | |
| 3,862,909 A | 1/1975 | Copeland | |
| 4,000,417 A | 12/1976 | Adkisson et al. | |
| 4,079,248 A | 3/1978 | Lehureau et al. | |
| 4,089,989 A * | 5/1978 | White | G01N 1/312 427/2.11 |
| 4,148,752 A | 4/1979 | Burger et al. | |
| 4,404,683 A | 9/1983 | Kobayashi et al. | |
| 4,477,185 A | 10/1984 | Berger et al. | |
| 4,595,829 A | 6/1986 | Neumann et al. | |

(Continued)

FOREIGN PATENT DOCUMENTS

| | | |
|---|---|---|
| CA | 2504245 | 11/2006 |
| CN | 102841079 | 12/2012 |

(Continued)

OTHER PUBLICATIONS

Sakura Finetek U.S.A., Inc., Final office action dated Sep. 2, 2014 for Japanese App No. 2011-553548.

(Continued)

*Primary Examiner* — William R Alexander
*Assistant Examiner* — Jeffrey Madonna
(74) *Attorney, Agent, or Firm* — Womble Bond Dickinson (US) LLP

(57) ABSTRACT

A microscope and methods of using the microscope to image a specimen on a microscope slide are disclosed. More particularly, embodiments of a microscope receive a slide carrier that loosely supports a plurality of microscope slides. The microscope may include a slide clamping assembly that clamps the plurality of microscope slides to fixedly support and physically separate the microscope slides from the slide carrier during imaging.

4 Claims, 25 Drawing Sheets

(56) References Cited

U.S. PATENT DOCUMENTS

| | | | |
|---|---|---|---|
| 4,673,988 A | 6/1987 | Jansson et al. | |
| 4,684,799 A | 8/1987 | Emoto et al. | |
| 4,737,022 A | 4/1988 | Faltermeier et al. | |
| 4,760,385 A | 7/1988 | Jansson et al. | |
| 4,761,075 A | 8/1988 | Matsushita et al. | |
| 4,836,667 A | 6/1989 | Ozeki | |
| 4,849,177 A * | 7/1989 | Jordan | B01L 3/508 206/521.7 |
| 4,958,920 A | 9/1990 | Jorgens et al. | |
| 4,962,264 A | 10/1990 | Forester | |
| 5,180,606 A * | 1/1993 | Stokes | G01N 1/312 118/314 |
| 5,287,272 A | 2/1994 | Rutenberg et al. | |
| 5,297,034 A | 3/1994 | Weinstein | |
| 5,297,215 A | 3/1994 | Yamagishi | |
| 5,311,426 A * | 5/1994 | Donohue | B01L 3/545 356/39 |
| 5,367,401 A * | 11/1994 | Saulietis | G01N 35/00029 356/246 |
| 5,428,690 A | 6/1995 | Bacus et al. | |
| 5,473,706 A | 12/1995 | Bacus et al. | |
| 5,530,237 A | 6/1996 | Sato et al. | |
| 5,532,874 A * | 7/1996 | Stein | G02B 21/0024 359/368 |
| 5,546,323 A | 8/1996 | Bacus et al. | |
| 5,561,556 A | 10/1996 | Weissman et al. | |
| 5,581,637 A | 12/1996 | Cass et al. | |
| 5,655,028 A | 8/1997 | Soll et al. | |
| 5,659,174 A | 8/1997 | Kaneoka et al. | |
| 5,675,141 A | 10/1997 | Kukihara | |
| 5,696,589 A | 12/1997 | Bernacki | |
| 5,737,084 A | 4/1998 | Ishihara | |
| 5,768,033 A * | 6/1998 | Brock | G02B 21/0008 359/813 |
| 5,793,969 A | 8/1998 | Kamentsky et al. | |
| 5,836,877 A | 11/1998 | Zavislan | |
| 5,864,138 A | 1/1999 | Miyata et al. | |
| 5,891,619 A | 4/1999 | Zakim et al. | |
| 5,924,074 A | 6/1999 | Evans | |
| 5,947,167 A * | 9/1999 | Bogen | B01L 3/0293 141/1 |
| 6,008,892 A | 12/1999 | Kain et al. | |
| 6,031,930 A | 2/2000 | Bacus et al. | |
| 6,043,475 A | 3/2000 | Shimada et al. | |
| 6,061,176 A | 5/2000 | Shih | |
| 6,078,681 A | 6/2000 | Silver | |
| 6,091,075 A | 7/2000 | Shibata et al. | |
| 6,091,842 A | 7/2000 | Domanik et al. | |
| 6,101,265 A | 8/2000 | Bacus et al. | |
| 6,130,745 A | 10/2000 | Manian et al. | |
| 6,147,797 A | 11/2000 | Lee | |
| 6,205,235 B1 | 3/2001 | Roberts | |
| 6,208,374 B1 | 3/2001 | Clinch | |
| 6,215,892 B1 | 4/2001 | Douglass et al. | |
| 6,226,352 B1 | 5/2001 | Salb | |
| 6,226,392 B1 | 5/2001 | Bacus et al. | |
| 6,248,995 B1 | 6/2001 | Tanaami et al. | |
| 6,272,235 B1 | 8/2001 | Bacus et al. | |
| 6,309,607 B1 * | 10/2001 | Johnston | G01N 1/312 118/423 |
| 6,396,941 B1 | 5/2002 | Bacus et al. | |
| 6,404,906 B2 | 6/2002 | Bacus et al. | |
| 6,466,690 B2 | 10/2002 | Bacus et al. | |
| 6,522,774 B1 | 2/2003 | Bacus et al. | |
| 6,529,271 B1 | 3/2003 | Engelhardt | |
| 6,606,413 B1 | 8/2003 | Zeineh | |
| 6,671,393 B2 | 12/2003 | Hays et al. | |
| 6,674,881 B2 | 1/2004 | Bacus et al. | |
| 6,674,884 B2 | 1/2004 | Bacus et al. | |
| 6,678,398 B2 | 1/2004 | Wolters et al. | |
| 6,684,092 B2 | 1/2004 | Zavislan | |
| 6,711,283 B1 | 3/2004 | Soenksen | |
| 6,735,531 B2 | 5/2004 | Rhett et al. | |
| 6,775,402 B2 | 8/2004 | Bacus et al. | |
| 6,800,249 B2 | 10/2004 | de la Torre-Bueno | |
| 6,800,853 B2 | 10/2004 | Ohkura | |
| 6,812,446 B2 | 11/2004 | Kreh | |
| 6,834,237 B2 | 12/2004 | Noergaard et al. | |
| 6,838,650 B1 | 1/2005 | Toh | |
| 6,847,481 B1 | 1/2005 | Ludl et al. | |
| 6,847,729 B1 | 1/2005 | Clinch et al. | |
| 6,947,583 B2 | 9/2005 | Ellis et al. | |
| 6,959,720 B2 | 11/2005 | Kurihara et al. | |
| 6,982,741 B2 | 1/2006 | Fiedler | |
| 6,993,169 B2 | 1/2006 | Wetzel et al. | |
| 7,009,638 B2 | 3/2006 | Gruber et al. | |
| 7,016,109 B2 | 3/2006 | Nakagawa | |
| 7,027,627 B2 | 4/2006 | Levin et al. | |
| 7,031,507 B2 | 4/2006 | Bacus et al. | |
| 7,071,969 B1 | 7/2006 | Stimson | |
| 7,098,634 B1 | 8/2006 | Yu | |
| 7,110,586 B2 | 9/2006 | Bacus et al. | |
| 7,110,645 B2 | 9/2006 | Birk et al. | |
| 7,133,545 B2 | 11/2006 | Douglass et al. | |
| 7,136,518 B2 | 11/2006 | Griffin et al. | |
| 7,141,802 B2 | 11/2006 | Takeyama et al. | |
| 7,146,372 B2 | 12/2006 | Bacus et al. | |
| 7,149,332 B2 | 12/2006 | Bacus et al. | |
| 7,171,030 B2 | 1/2007 | Foran et al. | |
| 7,194,118 B1 | 3/2007 | Harris et al. | |
| 7,196,300 B2 | 3/2007 | Watkins et al. | |
| 7,209,287 B2 | 4/2007 | Lauer | |
| 7,212,660 B2 | 5/2007 | Wetzel et al. | |
| 7,224,839 B2 | 5/2007 | Zeineh | |
| 7,233,340 B2 | 6/2007 | Hughes et al. | |
| 7,248,403 B2 | 7/2007 | Nakagawa | |
| 7,250,963 B2 | 7/2007 | Yuri et al. | |
| 7,292,251 B1 | 11/2007 | Gu | |
| 7,297,910 B2 | 11/2007 | Fomitchov | |
| 7,301,133 B2 | 11/2007 | Weiss | |
| 7,349,482 B2 | 3/2008 | Kim | |
| 7,359,548 B2 | 4/2008 | Douglass et al. | |
| 7,391,894 B2 | 6/2008 | Zeineh | |
| 7,394,482 B2 | 7/2008 | Olschewski | |
| 7,394,979 B2 | 7/2008 | Luther et al. | |
| 7,396,508 B1 * | 7/2008 | Richards | G01N 1/312 141/145 |
| 7,400,342 B2 | 7/2008 | Gaida et al. | |
| 7,400,983 B2 | 7/2008 | Feingold et al. | |
| 7,406,215 B2 | 7/2008 | Clune et al. | |
| 7,421,102 B2 | 9/2008 | Wetzel et al. | |
| 7,426,345 B2 | 9/2008 | Takamatsu et al. | |
| 7,428,325 B2 | 9/2008 | Douglass et al. | |
| 7,433,026 B2 | 10/2008 | Wolpert et al. | |
| 7,456,377 B2 | 11/2008 | Zeineh et al. | |
| 7,463,761 B2 | 12/2008 | Eichhorn et al. | |
| 7,470,541 B2 * | 12/2008 | Copeland | B01F 5/0057 422/63 |
| 7,482,600 B2 | 1/2009 | Seyfried | |
| 7,483,554 B2 | 1/2009 | Kotsianti et al. | |
| 7,486,329 B2 | 2/2009 | Endo | |
| 7,502,519 B2 | 3/2009 | Eichhorn et al. | |
| 7,542,596 B2 | 6/2009 | Bacus et al. | |
| 7,550,699 B1 | 6/2009 | Marshall | |
| 7,584,019 B2 | 9/2009 | Feingold et al. | |
| 7,596,249 B2 | 9/2009 | Bacus et al. | |
| 7,602,524 B2 | 10/2009 | Eichhorn et al. | |
| 7,623,697 B1 | 11/2009 | Hughes et al. | |
| 7,630,113 B2 | 12/2009 | Sase et al. | |
| 7,633,616 B2 | 12/2009 | Hing | |
| 7,642,093 B2 | 1/2010 | Tseung et al. | |
| 7,653,300 B2 | 1/2010 | Fujiyoshi et al. | |
| 7,657,070 B2 | 2/2010 | Lefebvre | |
| 7,663,078 B2 | 2/2010 | Virag et al. | |
| 7,677,289 B2 | 3/2010 | Hayworth et al. | |
| 7,689,024 B2 | 3/2010 | Eichhorn et al. | |
| 7,738,688 B2 | 6/2010 | Eichhorn et al. | |
| 7,756,309 B2 | 7/2010 | Gholap et al. | |
| 7,756,357 B2 | 7/2010 | Yoneyama | |
| 7,778,485 B2 | 8/2010 | Zeineh et al. | |
| 7,822,257 B2 | 10/2010 | Endo et al. | |
| 7,840,300 B2 | 11/2010 | Harker | |
| 7,856,131 B2 | 12/2010 | Bacus et al. | |

(56) References Cited

U.S. PATENT DOCUMENTS

| | | |
|---|---|---|
| 7,860,292 B2 | 12/2010 | Eichhorn et al. |
| 7,864,414 B2 | 1/2011 | Sase et al. |
| 7,869,641 B2 | 1/2011 | Wetzel et al. |
| 7,873,193 B2 | 1/2011 | De La Torre-Bueno et al. |
| 7,876,948 B2 | 1/2011 | Wetzel et al. |
| RE42,220 E | 3/2011 | Clinch et al. |
| 7,901,941 B2 | 3/2011 | Tseung et al. |
| 7,912,267 B2 | 3/2011 | Kawano et al. |
| 7,916,916 B2 | 3/2011 | Zeineh |
| 7,920,163 B1 | 4/2011 | Kossin |
| 7,925,067 B2 | 4/2011 | Bacus et al. |
| 7,944,608 B2 | 5/2011 | Hayashi et al. |
| 7,949,161 B2 | 5/2011 | Kawanabe et al. |
| 7,957,057 B2 | 6/2011 | Sase et al. |
| 7,967,057 B2 | 6/2011 | Kunii et al. |
| 7,978,894 B2 | 7/2011 | Soenksen et al. |
| 8,000,560 B2 | 8/2011 | Shirota |
| 8,000,562 B2 | 8/2011 | Morales et al. |
| 8,036,868 B2 | 10/2011 | Zeineh et al. |
| 8,074,547 B2 | 12/2011 | Ito et al. |
| 8,077,959 B2 | 12/2011 | Dekel et al. |
| 8,085,296 B2 | 12/2011 | Yuguchi et al. |
| 8,094,902 B2 | 1/2012 | Crandall et al. |
| 8,094,914 B2 | 1/2012 | Iki et al. |
| 8,098,279 B2 | 1/2012 | Sase et al. |
| 8,098,956 B2 | 1/2012 | Tatke et al. |
| 8,103,082 B2 | 1/2012 | Olson et al. |
| 8,125,534 B2 | 2/2012 | Shimonaka |
| 8,159,547 B2 | 4/2012 | Kawashima |
| 8,174,763 B2 | 5/2012 | Guiney et al. |
| 8,187,536 B2 | 5/2012 | Graupner et al. |
| 8,199,358 B2 | 6/2012 | Eichhorn et al. |
| 8,203,575 B2 | 6/2012 | Molnar et al. |
| 8,283,176 B2 | 10/2012 | Bland et al. |
| 8,304,704 B2 | 11/2012 | Hing et al. |
| 8,305,434 B2 | 11/2012 | Nakatsuka et al. |
| 8,306,298 B2 | 11/2012 | Bacus et al. |
| 8,306,300 B2 | 11/2012 | Bacus et al. |
| 8,339,703 B2 | 12/2012 | Knebel |
| 8,350,904 B2 | 1/2013 | Fujimoto et al. |
| 8,366,857 B2 | 2/2013 | Hayworth et al. |
| 8,385,619 B2 | 2/2013 | Soenksen |
| 8,385,686 B2 | 2/2013 | Sano |
| 8,388,891 B2 | 3/2013 | Lefebvre |
| 8,394,635 B2 | 3/2013 | Key et al. |
| 8,396,669 B2 | 3/2013 | Cocks |
| 8,463,741 B2 | 6/2013 | Ehlke et al. |
| 8,473,035 B2 | 6/2013 | Frangioni |
| 8,476,585 B2 | 7/2013 | Galloway |
| 8,501,435 B2 | 8/2013 | Gustafsson et al. |
| 8,565,480 B2 | 10/2013 | Eichhorn et al. |
| 8,565,503 B2 | 10/2013 | Eichhorn et al. |
| 8,582,489 B2 | 11/2013 | Eichhorn et al. |
| 8,582,849 B2 | 11/2013 | Eichhorn et al. |
| 8,673,642 B2 | 3/2014 | Key et al. |
| 8,687,858 B2 | 4/2014 | Walter et al. |
| 8,725,237 B2 | 5/2014 | Bryant-Greenwood et al. |
| 8,730,315 B2 | 5/2014 | Yoneyama |
| 8,744,213 B2 | 6/2014 | Tatke et al. |
| 8,747,746 B2 | 6/2014 | Lefebvre |
| 8,771,978 B2 | 7/2014 | Ragan |
| 8,788,217 B2 | 7/2014 | Feingold et al. |
| 8,796,038 B2 | 8/2014 | Williamson, IV et al. |
| 8,827,760 B2 | 9/2014 | Ushibo et al. |
| 8,923,597 B2 | 12/2014 | Eichhorn et al. |
| 2001/0035752 A1 | 11/2001 | Kormos et al. |
| 2002/0169512 A1 | 11/2002 | Stewart |
| 2002/0176160 A1 | 11/2002 | Suzuki et al. |
| 2002/0176161 A1 | 11/2002 | Yoneyama et al. |
| 2003/0048931 A1 | 3/2003 | Johnson et al. |
| 2003/0098921 A1 | 5/2003 | Endo |
| 2003/0112330 A1 | 6/2003 | Yuri et al. |
| 2003/0112504 A1 | 6/2003 | Czarnetzki et al. |
| 2003/0124729 A1* | 7/2003 | Christensen ............ G01N 1/30 436/43 |
| 2003/0133009 A1 | 7/2003 | Brown |
| 2003/0142882 A1 | 7/2003 | Beged-Dov et al. |
| 2003/0156276 A1 | 8/2003 | Bowes |
| 2004/0021936 A1 | 2/2004 | Czarnetzki et al. |
| 2004/0027462 A1 | 2/2004 | Hing |
| 2004/0090667 A1 | 5/2004 | Gartner et al. |
| 2004/0113043 A1 | 6/2004 | Ishikawa et al. |
| 2004/0129858 A1 | 7/2004 | Czarnetzki et al. |
| 2004/0135061 A1 | 7/2004 | Kreh |
| 2004/0141660 A1 | 7/2004 | Barth et al. |
| 2005/0057812 A1 | 3/2005 | Raber |
| 2005/0073649 A1 | 4/2005 | Spector |
| 2005/0094262 A1 | 5/2005 | Spediacci et al. |
| 2005/0112537 A1 | 5/2005 | Wu |
| 2005/0211874 A1 | 9/2005 | Takeyama et al. |
| 2005/0219688 A1 | 10/2005 | Kawano et al. |
| 2005/0221351 A1 | 10/2005 | Jekwam |
| 2005/0239113 A1 | 10/2005 | Ryu et al. |
| 2005/0248837 A1 | 11/2005 | Sase |
| 2005/0258335 A1 | 11/2005 | Oshiro et al. |
| 2006/0039583 A1 | 2/2006 | Bickert et al. |
| 2006/0045388 A1 | 3/2006 | Zeineh |
| 2006/0077536 A1 | 4/2006 | Bromage et al. |
| 2006/0088940 A1 | 4/2006 | Feingold et al. |
| 2006/0098861 A1 | 5/2006 | See et al. |
| 2006/0146283 A1 | 7/2006 | Baumann et al. |
| 2006/0164623 A1 | 7/2006 | Wagner et al. |
| 2006/0171560 A1 | 8/2006 | Manus |
| 2006/0179992 A1 | 8/2006 | Kermani |
| 2007/0025606 A1 | 2/2007 | Gholap et al. |
| 2007/0091324 A1 | 4/2007 | Paul et al. |
| 2007/0098237 A1 | 5/2007 | Yoo et al. |
| 2007/0102620 A1 | 5/2007 | Bublitz et al. |
| 2007/0164194 A1 | 7/2007 | Kurata et al. |
| 2007/0198001 A1 | 8/2007 | Bauch et al. |
| 2007/0207061 A1 | 9/2007 | Yang et al. |
| 2007/0285768 A1 | 12/2007 | Kawanabe et al. |
| 2008/0002252 A1 | 1/2008 | Weiss et al. |
| 2008/0020128 A1 | 1/2008 | van Ryper et al. |
| 2008/0054156 A1 | 3/2008 | Fomitchov |
| 2008/0095467 A1 | 4/2008 | Olszak et al. |
| 2008/0142708 A1 | 6/2008 | Workman et al. |
| 2008/0180794 A1 | 7/2008 | Tafas et al. |
| 2008/0240613 A1 | 10/2008 | Dietz et al. |
| 2008/0283722 A1 | 11/2008 | Uchiyama et al. |
| 2009/0040322 A1 | 2/2009 | Leberl et al. |
| 2009/0046298 A1 | 2/2009 | Betzig |
| 2009/0116101 A1 | 5/2009 | Tafas et al. |
| 2009/0140169 A1 | 6/2009 | Niehren |
| 2009/0195688 A1 | 8/2009 | Henderson |
| 2010/0000383 A1 | 1/2010 | Koos et al. |
| 2010/0020157 A1 | 1/2010 | Jelinek et al. |
| 2010/0039507 A1 | 2/2010 | Imade |
| 2010/0074489 A1 | 3/2010 | Bacus et al. |
| 2010/0093022 A1 | 4/2010 | Hayworth et al. |
| 2010/0102571 A1 | 4/2010 | Yang |
| 2010/0109725 A1 | 5/2010 | Yun et al. |
| 2010/0118393 A1 | 5/2010 | Lin |
| 2010/0134655 A1 | 6/2010 | Kuroiwa |
| 2010/0141751 A1 | 6/2010 | Uchida |
| 2010/0141752 A1 | 6/2010 | Yamada |
| 2010/0141753 A1 | 6/2010 | Olson et al. |
| 2010/0171809 A1 | 7/2010 | Fujiyoshi |
| 2010/0177166 A1 | 7/2010 | Eichhorn et al. |
| 2010/0188738 A1 | 7/2010 | Epple et al. |
| 2010/0194873 A1 | 8/2010 | Viereck et al. |
| 2010/0201800 A1 | 8/2010 | Yamamoto et al. |
| 2010/0225668 A1 | 9/2010 | Tatke et al. |
| 2010/0260407 A1 | 10/2010 | Eichhorn et al. |
| 2010/0279342 A1 | 11/2010 | Kijima et al. |
| 2010/0295932 A1 | 11/2010 | Yakomachi et al. |
| 2010/0310139 A1 | 12/2010 | Kimura |
| 2011/0017902 A1 | 1/2011 | Hing et al. |
| 2011/0037847 A1 | 2/2011 | Soenksen |
| 2011/0038523 A1 | 2/2011 | Boardman |
| 2011/0043663 A1 | 2/2011 | Tsuchiya |
| 2011/0064296 A1 | 3/2011 | Dixon |
| 2011/0074817 A1 | 3/2011 | Shinichi et al. |
| 2011/0102571 A1 | 5/2011 | Yoneyama |

(56) References Cited

U.S. PATENT DOCUMENTS

| | | |
|---|---|---|
| 2011/0109735 A1 | 5/2011 | Otsuka |
| 2011/0145755 A1 | 6/2011 | Bacus et al. |
| 2011/0181622 A1 | 7/2011 | Bacus et al. |
| 2011/0221881 A1 | 9/2011 | Shirota et al. |
| 2011/0316993 A1 | 12/2011 | Chen et al. |
| 2011/0316999 A1 | 12/2011 | Yoneyama et al. |
| 2012/0002043 A1 | 1/2012 | Nitta |
| 2012/0002892 A1 | 1/2012 | Eichhorn et al. |
| 2012/0038979 A1 | 2/2012 | Hing et al. |
| 2012/0044342 A1 | 2/2012 | Hing et al. |
| 2012/0069171 A1 | 3/2012 | Kodaira et al. |
| 2012/0069344 A1 | 3/2012 | Liu |
| 2012/0076391 A1 | 3/2012 | Dietz et al. |
| 2012/0076411 A1 | 3/2012 | Dietz et al. |
| 2012/0076436 A1 | 3/2012 | Dietz et al. |
| 2012/0081536 A1 | 4/2012 | Kuppig et al. |
| 2012/0114204 A1 | 5/2012 | Olson et al. |
| 2012/0120225 A1 | 5/2012 | Maddison |
| 2012/0127297 A1 | 5/2012 | Baxi et al. |
| 2012/0163680 A1 | 6/2012 | Lefebvre |
| 2012/0208184 A1 | 8/2012 | Ragan |
| 2012/0281931 A1 | 11/2012 | Eichhorn et al. |
| 2013/0003172 A1 | 1/2013 | Widzgowski et al. |
| 2013/0076886 A1 | 3/2013 | Ikeno et al. |
| 2013/0140459 A1 | 6/2013 | Galloway |
| 2013/0162802 A1 | 6/2013 | Soenksen |
| 2013/0164781 A1 | 6/2013 | Lefebvre |
| 2013/0182922 A1 | 7/2013 | Kil |
| 2013/0216451 A1 | 8/2013 | Hayworth et al. |
| 2013/0250090 A1 | 9/2013 | Morimoto |
| 2014/0030757 A1 | 1/2014 | Schiffenbauer |
| 2014/0049632 A1 | 2/2014 | Hemmer |
| 2014/0051158 A1 | 2/2014 | Nakajima et al. |
| 2014/0085453 A1 | 3/2014 | Yamane |
| 2014/0086463 A1 | 3/2014 | Meetz et al. |
| 2014/0087411 A1 | 3/2014 | Chow et al. |
| 2014/0098376 A1 | 4/2014 | Hashimshony et al. |
| 2014/0112560 A1 | 4/2014 | Soenksen |
| 2014/0118528 A1 | 5/2014 | Wolff et al. |
| 2014/0130613 A1 | 5/2014 | Adiga et al. |
| 2014/0137715 A1 | 5/2014 | Sneyders et al. |
| 2015/0015578 A1 | 1/2015 | Eichhorn et al. |
| 2015/0153552 A1 | 6/2015 | Loney et al. |
| 2015/0153555 A1 | 6/2015 | Loney et al. |
| 2015/0153556 A1 | 6/2015 | Loney et al. |

FOREIGN PATENT DOCUMENTS

| | | |
|---|---|---|
| DE | 102009012293 | 3/2009 |
| EP | 1447699 | 8/2004 |
| EP | 2051051 | 4/2009 |
| EP | 2110696 | 10/2009 |
| EP | 2169379 A2 | 3/2010 |
| EP | 2169379 A3 | 6/2015 |
| FR | 2620537 | 3/1989 |
| GB | 03092 | 11/1906 |
| JP | 59071018 | 4/1984 |
| JP | 61248168 | 11/1986 |
| JP | S63206793 | 8/1988 |
| JP | 09080138 | 3/1997 |
| JP | 09133856 | 5/1997 |
| JP | 09161068 | 6/1997 |
| JP | 09218354 | 8/1997 |
| JP | 2001281553 | 10/2001 |
| JP | 2002031513 | 1/2002 |
| JP | 200284554 | 3/2002 |
| JP | 2006003543 | 1/2006 |
| JP | 2006343595 | 12/2006 |
| JP | 2009192824 | 2/2008 |
| JP | 2008262100 | 10/2008 |
| TW | 201201392 | 1/2012 |
| WO | WO-0154052 | 7/2001 |
| WO | WO-2005015120 | 2/2005 |
| WO | WO-2008118886 | 10/2008 |
| WO | WO-2008141009 | 11/2008 |
| WO | WO-2010105015 | 9/2010 |
| WO | WO-2012024627 | 2/2012 |

OTHER PUBLICATIONS

Sakura Finetek U.S.A., Inc., Examination Report dated Jun. 19, 2014 for Australian App No. 2011291517.

Sakura Finetek U.S.A., Inc., PCT Search Report and Written Opinion dated Sep. 22, 2014 for International Application No. PCT/US2014/034477, 12 pages.

Sakura Finetek U.S.A., Inc., Chinese Final Office Action dated Sep. 22, 2014 for CN Application No. 201080017649.4.

Sakura Finetek U.S.A., Inc., et al., European Office Action dated Jan. 30, 2015 for EP App. No. 11749675.2.

Sakura Finetek U.S.A., Inc., Non final office action dated Apr. 8, 2015 for U.S. Appl. No. 13/255,827.

Sakura Finetek U.S.A., Inc., Final office action dated Apr. 15, 2015 for U.S. Appl. No. 13/212,955.

Sakura Finetek U.S.A., Inc., et al., Australian Examination Report dated Feb. 2, 2015 for App No. 2011291517.

Sakura Finetek U.S.A., Inc., et al., Chinese Office Action dated Nov. 15, 2014 for CN 201180047558.X.

Sakura Finetek U.S.A., Inc., European second office action dated Nov. 6, 2014 for EP Appln. No. 10719379.9.

Sakura Finetek U.S.A., Inc. Partial European search report for Application No. 14198636.4, dated Apr. 28, 2015.

Sakura Finetek USA, Extended Search Report for EP15154503 dated Jun. 19, 2015.

Sakura Finetek U.S.A., Inc., Chinese second office action dated Dec. 27, 2013 for CN201080017649.4.

Sakura Finetek U.S.A., Extended Search Report for EP14198636, dated Sep. 30, 2015.

Forrest, K., et al., "Tunneling calculations for GaAs—AlxGa(1-x)As graded band-gap sawtooth superlattices", IEEE Journal of Quantum Electronics, vol. 26, No. 6, (Jun. 1990), 1067-1074.

Sakura Finetek U.S.A., Inc., "Non-Final Office Action", U.S. Appl. No. 13/212,955, (dated May 3, 2016).

Haruhisa, S., et al., "Application of telepathology for improvement of therapeutic effects and economic efficiency, and development of new equipment for it", Science Links Japan; http://sciencelinks.jp/j-east/article/200516/000020051605A0431066.php, Journal Code: N20051113, (2005), 166-125.

Sakura Finetek U.S.A., Inc., PCT Search Report and Written Opinion dated Oct. 13, 2011 for Int'l Application No. PCT/US2011/048488, 13 pages.

Sakura Finetek U.S.A., Inc., EPO Office Action dated Jul. 30, 2013 for EPO App No. 10719379.9, 8 pages.

Sakura Finetek U.S.A., Inc., Australian Office Action dated Nov. 26, 2013 for Australian App No. 2010222633, 3 pages.

Sakura Finetek U.S.A., Inc., Japanese Office Action dated Dec. 10, 2013 for JP App No. P2011-553548, 9 pages.

Sakura Finetek U.S.A., Inc., et al., Canadian Examiner's Report dated Dec. 7, 2012 for CA 2,755,164.

Sakura Finetek U.S.A., Inc., et al., International Preliminary Report on Patentability dated Mar. 7, 2013 for PCT/US2011/048488.

Sakura Finetek U.S.A., Inc., et al., Australian Examination Report dated Dec. 24, 2013 for AU 2011291517.

Sensovation AG, PCT International Preliminary Report on Patentability dated Sep. 20, 2011 for Int'l Application No. PCT/IB2010/000518, 7 pages.

Sakura Finetek U.S.A., Inc., "EP Supplementary Search Report", EP Application No. 14784707.3, (dated Oct. 4, 2016).

Sakura Finetek U.S.A., Inc., "Examination Report", CA Application No. 2908058, (dated Nov. 16, 2016).

Sakura Finetek U.S.A., Inc., "Extended European Search Report", EP Application No. 15194968.2, (dated Mar. 18, 2016).

Sakura Finetek U.S.A., Inc., "Final office action", U.S. Appl. No. 13/212,955, (dated Oct. 31, 2016).

Sakura Finetek U.S.A., Inc., "Final Rejection", JP Application No. P2013-525005, (dated Dec. 27, 2016).

(56) References Cited

OTHER PUBLICATIONS

Sakura Finetek U.S.A., Inc., "First Office Action with search report", CN Application No. 2014800218372, (dated Nov. 30, 2016).
Sakura Finetek U.S.A., Inc., "Fourth Office Action", CN Application No. 201180047558X, (dated Oct. 24, 2016).
Sakura Finetek U.S.A., Inc., "International Preliminary Report on Patentability", PCT Application No. PCT/US2014/034477, (dated Oct. 29, 2015).
Sakura Finetek U.S.A., Inc., "International Search Report and Written Opinion", PCT Application No. PCT/US2014/034477, (dated Sep. 22, 2014).
Sakura Finetek U.S.A., Inc., "Non-Final Office Action", U.S. Appl. No. 14/779,550, (dated Jan. 19, 2017).
Sakura Finetek U.S.A., Inc., "Notice of rejection", JP Application No. 2013-525005, (dated Feb. 9, 2016).
Sakura Finetek U.S.A., Inc., "Patent Examination Report No. 1", AU Application No. 201453889, (dated May 18, 2016).
Sakura Finetek U.S.A., Inc., "Second office action", CN Application No. 201180047558.X, (dated Jul. 6, 2015).
Sakura Finetek U.S.A., Inc., "Third Office Action", CN Application No. 201180047558X, (dated Apr. 1, 2016).
Sakura Finetek USA Inc., "Office Action", EP Application No. 15154503.5, (dated Feb. 28, 2017).
Sakura Finetek USA, Inc., "Office Action", JP Application No. 2016-507909, (dated Sep. 15, 2016).
Sakura Finetek U.S.A., Inc., "First Office Action", EP Application No. 15194968.2, (dated Mar. 10, 2017).
Sakura Finetek U.S.A., Inc., "Examiner's Report", CA Application No. 2808105, dated Jun. 12, 2017.
Sakura Finetek U.S.A., Inc., "Examiner's Report", CA Application No. 2908058, dated Jul. 24, 2017.
Sakura Finetek U.S.A., Inc., "Final Office Action", JP Application No. 2016-507909, dated Apr. 28, 2017.
Sakura Finetek U.S.A., Inc., "Final Office Action", U.S. Appl. No. 14/779,550, dated May 24, 2017.
Sakura Finetek U.S.A., Inc., "Non final office action", U.S. Appl. No. 13/212,955, dated Aug. 9, 2017.
Sakura Finetek U.S.A., Inc., "Second Office Action", CN Application No. 2014800218372, dated Aug. 1, 2017.

* cited by examiner

SECTION A-A

SECTION B-B

SECTION C-C

SECTION D-D

DETAIL A

DETAIL B

DETAIL C

DETAIL D

DETAIL E

DETAIL F

MICROSCOPE WITH SLIDE CLAMPING ASSEMBLY

BACKGROUND

Field

Holding devices, particularly for use with imaging devices, are disclosed. More particularly, embodiments relate to slide carriers, such as slide carriers for use with microscopes used for imaging microscope slides.

Background Information

The examination of biological specimens is sometimes required for diagnostic purposes. Generally speaking, pathologists and other diagnosticians utilize microscopes, such as digital microscopes, to study histological specimens from patients. Histological examination of specimens may include numerous steps, such as the collection and processing of biological samples onto microscope slides, sorting of prepared microscope slides according to tissue origin, e.g., according to a patient identifier, transportation of sorted microscope slides to a pathologist for viewing, and finally various stages of imaging and analysis prior to storing the samples for future reference.

The viewing of a biological sample on a microscope slide generally involves magnification of a region of interest of the sample. Traditionally, this is done by imaging the region of interest through a microscope, e.g., by capturing an image with a digital microscope and displaying the image on a display monitor. However, existing microscopes have capacity constraints that prevent the user from examining a large number of microscope slides simultaneously, i.e., during a single examination session, without reloading the microscope with new slides. Furthermore, existing microscopes that permit multiple microscope slides to be loaded simultaneously require the user to transfer slides individually from a transportation container to the microscope, resulting in extended loading times. Existing multi-slide microscopes also utilize widely-spaced slide positions, causing delays when switching views from a first slide to a second slide. Additionally, current methods of storing and archiving slides after examination often require repacking of the examined slides, which can be time consuming and may result in slide misplacement.

SUMMARY

Holding devices, particularly for use with imaging devices, are disclosed. In an embodiment, a microscope slide carrier includes a carrier body and a plurality of slide receptacles. The carrier body may have an upper surface perpendicular to a longitudinal axis and a central opening through the carrier body along the longitudinal axis. The plurality of slide receptacles may be circumferentially spaced about the longitudinal axis in the upper surface. Each slide receptacle may include an outer profile extending partially through the carrier body and a support within the outer profile. The outer profile may be configured to loosely receive a microscope slide and the support may be configured to support the received microscope slide.

In an embodiment, each slide receptacle includes an inner profile radially offset from the central opening and extending fully through the carrier body within the outer profile. Furthermore, one or more tooth may extend radially from a wall of the carrier body. For example, one or more tooth may extend radially inward from an inner wall of the carrier body, or one or more tooth may extend radially outward from an outer wall of the carrier body.

In an embodiment, a microscope includes an image sensor, a clamp member, and a clamp hub. The clamp member may have a plurality of clamp surfaces circumferentially spaced about a longitudinal axis and each clamp surface may be perpendicular to the longitudinal axis. The clamp hub may have a plurality of clamp seats circumferentially arranged with a same spacing about the longitudinal axis as the plurality of clamp surfaces. In an embodiment, each clamp surface may pair with a respective clamp seat and be located a same longitudinal distance from a paired clamp seat. Accordingly, a plurality of microscope slides between the pairs of clamp surfaces and clamp seats may be simultaneously clamped when the clamp member is moved toward the clamp hub in a longitudinal direction.

In an embodiment, the clamp member may include a clamp plate and a plurality of fingers, and each finger may cantilever from the clamp plate toward a respective clamp surface. The microscope may also include a plurality of clamp nubs, and each clamp nub may be coupled with a respective finger. The plurality of clamp surfaces may be located on the plurality of nubs. In an embodiment, the plurality of cantilevered fingers and the plurality of clamp nubs are resilient.

In an embodiment, the clamp hub includes a slide carrier receiver coaxially arranged with a slide seating plate. The slide carrier receiver may be located longitudinally between the clamp member and the slide seating plate. One or more tooth may extend radially from a bottom land of the slide carrier receiver. In an embodiment, the clamp hub includes a bushing extending longitudinally from the slide seating plate, and the slide carrier receiver is slidably positioned about the bushing. A biasing element may bias the slide carrier receiver longitudinally away from the slide seating plate. In an embodiment, each clamp seat includes one or more bosses extending in a longitudinal direction toward the clamp member, and each boss may have a distal surface area less than a surface area of the clamp seat.

In an embodiment, the microscope further includes a spindle having a shaft and a locking mechanism. The shaft may be coaxially aligned with the clamp member and the clamp hub. The locking mechanism may be configured to longitudinally couple the clamp member with the clamp hub. In an embodiment, the microscope may further include a motor coupled with the spindle to rotate the shaft about the longitudinal axis. In an embodiment, only one of either the clamp member or the clamp hub is fixed to the shaft. The microscope may also include an actuator connected with the spindle to actuate the locking mechanism such that the locking mechanism engages whichever of the clamp member or the clamp hub is not fixed to the shaft.

In an embodiment, the microscope may include a first linear stage connected with the spindle and a second linear stage connected with the spindle. The first linear stage may move the spindle in a first direction within a transverse plane perpendicular to the longitudinal axis. The second linear stage may move the spindle in a second direction within the transverse plane. The second direction may be perpendicular to the first direction.

In an embodiment, a method includes inserting a microscope slide into a slide receptacle of a microscope slide carrier such that the slide receptacle loosely supports the microscope slide with the microscope slide contacting the microscope slide carrier. The method may also include loading the microscope slide carrier into a microscope, and gripping the microscope slide between a clamp member and a clamp hub of the microscope such that, in response to the gripping, the microscope fixedly supports the microscope slide with the microscope slide separated apart from the microscope slide carrier. The method may include rotating the loaded microscope slide about a longitudinal axis while the microscope slide carrier remains rotationally fixed relative to the microscope slide. The method may also include sensing an image of a target area on the microscope slide with an image sensor of the microscope. The target area may include a label on the microscope slide.

In an embodiment, the method includes moving the gripped microscope slide in one or more transverse direction perpendicular to the longitudinal axis, wherein the target area includes a specimen on the microscope slide. Gripping the microscope slide may include meshing one or more tooth of the microscope slide carrier with one or more tooth of the clamp hub. Gripping the microscope slide may also include actuating a locking mechanism to longitudinally couple the clamp member with the clamp hub while the microscope slide is gripped between a clamp surface of the clamp member and a clamp seat of the clamp hub.

In an embodiment, the method may include inserting a second microscope slide into a second slide receptacle of the microscope slide carrier such that the second slide receptacle loosely supports the second microscope slide with the second microscope slide contacting the microscope slide carrier. The method may also include gripping the second microscope slide between the clamp member and the clamp hub simultaneously with gripping the first microscope slide.

In an embodiment, a method includes gripping a plurality of microscope slides simultaneously to fixedly support the microscope slides in a circumferential pattern about a longitudinal axis. The method may also include imaging a first position on a first microscope slide of the plurality of microscope slides, rotating the plurality of microscope slides about the longitudinal axis, and imaging a second position on a second microscope slide of the plurality of microscope slides. Imaging the first position may include displaying a first video of the first position on a display. The first video may include a first plurality of images displayed at a first video rate of at least fifteen images per second. Imaging the first position may also include capturing a first image of the first plurality of images. The method may also include imaging a second position. Imaging the second position may include displaying a second video of the second position on the display. The second video may include a plurality of second images displayed at a second video rate of at least fifteen images per second. Imaging the second position may also include capturing a second image of the second plurality of images.

In an embodiment, the method may also include displaying the first image and the second image simultaneously on the display. Either the first image or the second image may be selected while the images are simultaneously displayed on the display, and in response to selecting either the first image or the second image, the respective first or second position on the microscope slide corresponding to the selected image may be imaged.

DETAILED DESCRIPTION

Figure 1:
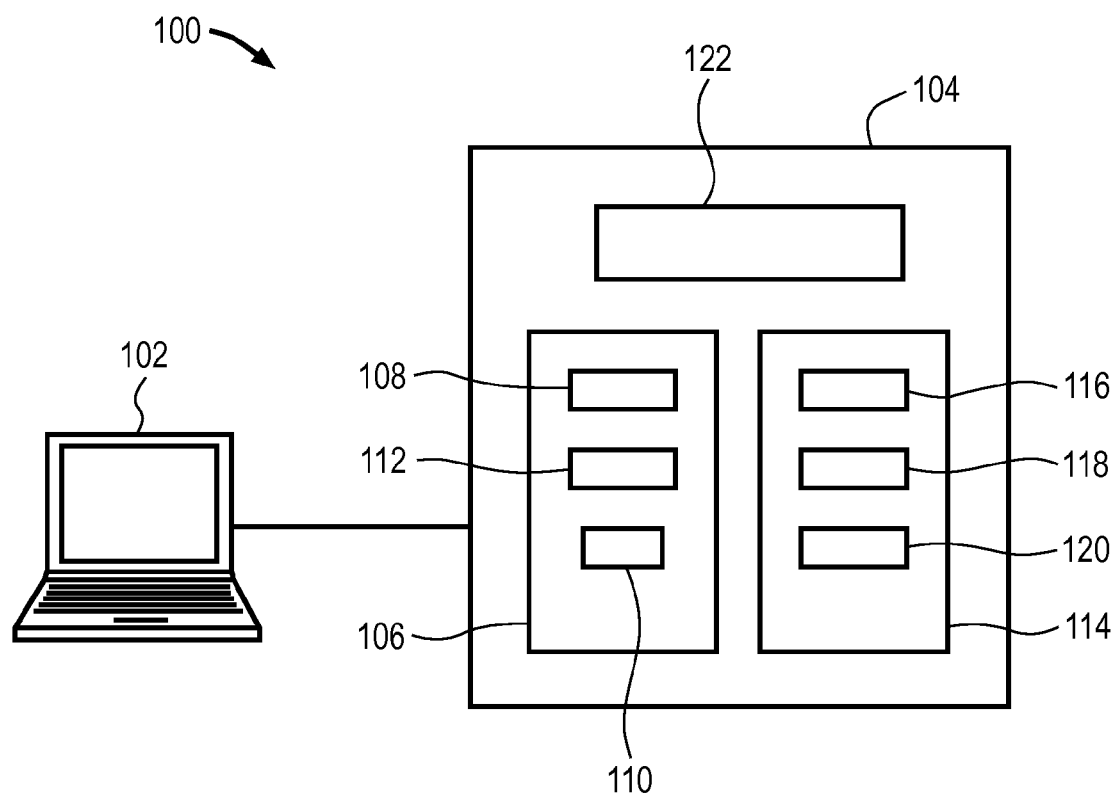
FIG. 1 is a block diagram of a microscopy system including a microscope for examining a specimen in accordance with an embodiment of the invention.

Embodiments describe microscopes and methods for imaging a specimen or specimens on a microscope slide. The microscope may include any of the microscope components illustrated and described in related U.S. Patent Publication No. 2012/0044342, filed on Aug. 18, 2011. While some embodiments are described with specific regard to a microscope having a slide clamping assembly used in combination with a slide carrier, the embodiments are not so limited and certain embodiments may also be applicable to other uses. For example, a slide carrier as described below may be used for other purposes, including as a component of, or in combination with, a slide projector. More particularly, a slide carrier having features as described below may also be used in other applications to allow an object to be transported and archived in a loosely supported configuration, but to be inspected in a fixedly supported configuration.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment", or the like, means that a particular feature, structure, configuration, or characteristic described is included in at least one embodiment. Thus, the appearances of the phrase "one embodiment," "an embodiment", or the like, in various places throughout this specification are not necessarily referring to the same embodiment. Furthermore, the particular features, structures, configurations, or characteristics may be combined in any suitable manner in one or more embodiments.

In an aspect, embodiments describe a microscope slide carrier for organizing and storing microscope slides throughout the preparation, transportation, imaging, and archiving processes. In an embodiment, a slide carrier is provided that is able to hold a large number of microscope slides, e.g., between about 4 and 40 microscope slides. The slides may, for example, belong to the same patient case or be required to be evaluated and compared simultaneously. The slide carrier may be used to transport and store microscope slides, but also may be loaded directly into a microscope for viewing. For example, in an embodiment, the slide carrier may be loaded into the microscope with the microscope slides loosely supported in slide receptacles. Then, prior to imaging, the microscope slides may be clamped and lifted out of the slide carrier by a slide clamping assembly of the microscope. Thus, during imaging the microscope slides and the slide carrier may be physically separated by the microscope, but following imaging, the microscope slides may be replaced into the slide carrier. A user may then remove the slide carrier with all slides in a similar orientation as when they were inserted into the microscope. Accordingly, a large number of slides may be prepared, transported, imaged, and archived without being transferred individually from a slide carrier into a microscope. Furthermore, since the microscope slide moves independently from the slide carrier during imaging, the slide carrier may fit the slides loosely and may be manufactured using high-volume, low-cost, and low-precision methods.

In another aspect, embodiments describe a microscope for imaging a specimen on a microscope slide. In an embodiment, the microscope includes a slide clamping assembly configured to or operable to clamp and lift a microscope slide from a slide carrier that the microscope slide rests within. The slide clamping assembly may include a clamp member with a plurality of fingers supporting clamp surfaces. The clamping assembly may also include a clamp hub with a plurality of clamp seats that may be longitudinally aligned with the clamp surfaces. In an embodiment, one or more microscope slide is clamped between the clamp surfaces and the clamp seats when the clamp hub is moved toward the clamp member, and simultaneously, the slide carrier physically separates from the microscope slide. Thus, one or more microscope slide may have a first configuration in which it is loosely supported within a slide carrier and a second configuration in which the microscope slide is firmly supported by a slide clamping assembly apart from the slide carrier. In a case where there are multiple microscope slides, the microscope slides may be simultaneously clamped and supported apart from the slide carrier in a pattern, e.g., in a circumferential pattern. As a result, the microscope slides may become fixed relative to the slide clamping assembly and thus may be moved with high precision since movement of the slides becomes independent from movement of the low precision slide carrier.

In an aspect, a microscope slide carrier remains longitudinally aligned with a plurality of microscope slides during an imaging process. In an embodiment, as a slide clamping assembly of a microscope grips a microscope slide and separates the microscope slide from a microscope slide carrier, one or more teeth on the microscope slide carrier engages one or more teeth on a clamp hub that grips the microscope slide. Thus, as the clamp hub rotates or moves within a transverse plane, both the microscope slide and the slide carrier travel with the clamp hub and remain longitudinally aligned, albeit spaced apart. Accordingly, although movement of the slide and the slide carrier is independent from one another, the slide carrier maintains the same orientation relative to the microscope slide throughout the imaging process and thus avoids misarrangement of the slides.

In an aspect, a microscope provides for rapid switching between imaging of multiple microscope slides associated with a microscope slide carrier. In an embodiment, the microscope slide carrier includes a disc form and a plurality of microscope slides are arranged circumferentially about a longitudinal axis of the disc. Accordingly, when switching from imaging a first microscope slide to imaging a second slide, e.g., a microscope slide circumferentially opposite the first microscope slide, a motor may rotate the microscope slide carrier about the longitudinal axis to quickly change the field of view to the second microscope slide.

Referring to FIG. 1, a block diagram of a microscopy system including a microscope for examining a specimen is shown in accordance with an embodiment. In an embodiment, microscopy system 100 includes computer 102 interfaced with microscope 104. In an embodiment, microscope 104 is a digital microscope. Accordingly, microscope 104 may include one or more imaging sub-systems 106 and each imaging sub-system 106 may further include image sensor 108, optics 110, e.g., lenses, mirrors, etc., and light source 112. Each imaging system may have a different optical resolution or range of resolution with magnification greater or less than 1.0. Embodiments of these imaging sub-systems 106 are discussed further below.

Microscope 104 may include one or more motion sub-systems 114 to move various components of microscope 104 during examination of a specimen. For example, in an embodiment, microscope 104 includes shelf motion sub-system 116 to receive a slide carrier and move the slide carrier toward a clamping assembly. Microscope 104 may also include clamp hub motion sub-system 118 and a clamp member motion sub-system 120 to provide for gripping of microscope slides loaded in the slide carrier as well as movement of the slide carrier and microscope slides relative to the various imaging sub-systems 106 for imaging. Embodiments of these motion sub-systems 114 are discussed further below.

In an embodiment, computer 102 directly controls imaging sub-systems 106 and motion sub-systems 114. Alternatively, in an embodiment, microscope 104 includes control unit 122 connected with computer 102. Control unit 122 may act as an intermediary between computer 102 and the various sub-systems of microscope 104 to control operation of microscope 104 based on signals received from computer 102. For example, control unit 122 representatively includes a memory in which a set or sets of non-transitory instructions may be stored. Such a set of instruction may be executed to control various motors of motion sub-systems 114 and/or images sensors 108, optics 110, and light sources 112 of imaging sub-systems 106. The memory component or a separately connected memory component may be operable or utilized to store data about the various sub-systems.

Figure 2:
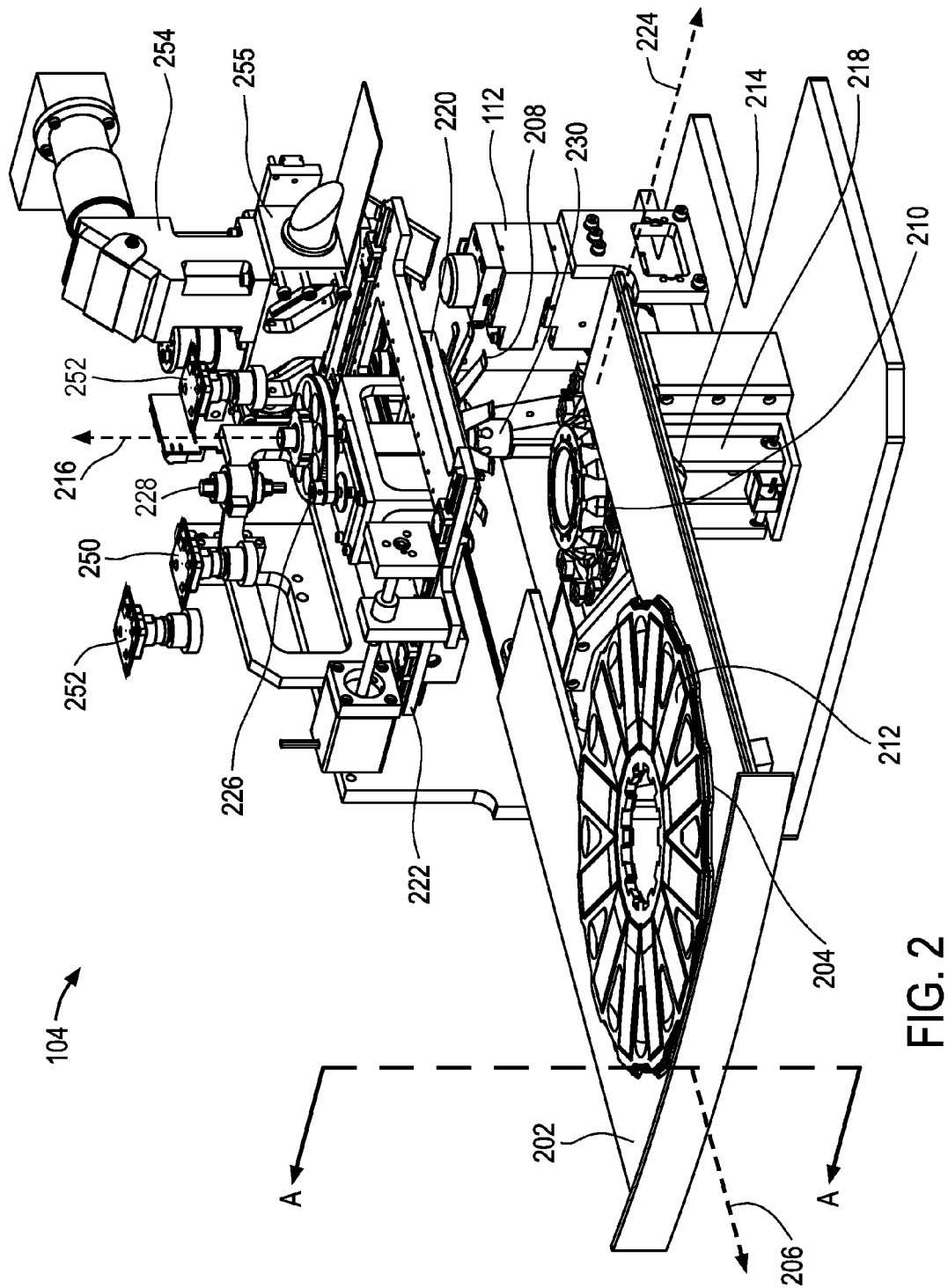
FIG. 2 is a perspective view of a microscope slide carrier loaded in a microscope in accordance with an embodiment of the invention.

Referring to FIG. 2, a perspective view of a microscope slide carrier loaded in a microscope is shown in accordance with an embodiment. In an embodiment, microscope 104 includes shelf 202 for receiving slide carrier 204 from a user. For example, a pathologist may manually place slide carrier 204 loaded with multiple, e.g., 4, 6, 10, 12, 40, etc., slides 212 onto shelf 202. Shelf 202 may include a perimeter contour that maintains slide carrier 204 in the same general rotational orientation by meshing with an outer perimeter contour of slide carrier 204. Shelf 202 may be configured to move along an x-axis 206 either manually or automatically under the control of a motor and under the axial constraint of linear slides. For example, a linear motor, pneumatic actuator, or hydraulic actuator of shelf motion sub-system 116 may be controlled to carry slide carrier 204 toward or away from a slide clamping assembly within microscope 104.

In an embodiment, a slide clamping assembly within microscope 104 includes clamp hub 210. Clamp hub motion sub-system 118 may control movement of clamp hub 210. For example, clamp hub 210 may connect with hub drive 214 that can rotate clamp hub 210 about longitudinal axis 216. In an embodiment, hub drive 214 is a stepper motor, although hub drive 214 may instead include a motor with rotational movement controlled with feedback from a rotary encoder. Hub drive 214 may also be connected with z-stage 218 that moves hub drive 214, and thus clamp hub 210, vertically along longitudinal axis 216. Z-stage 218 may be driven by a linear motor, pneumatic actuator, hydraulic actuator, or the like. Thus, clamp hub 210 may be provided with at least two degrees of freedom, including axial and rotational motion about longitudinal axis 216. Additional degrees of freedom may be achieved with more actuators.

In an embodiment, the clamping assembly also includes clamp member 208. Clamp member motion sub-system 120 may control movement of clamp member 208. For example, clamp member 208 may be connected with x-stage 220 that can move clamp member 208 is parallel to x-axis 206. In an embodiment, x-stage 220 and y-stage 222 may be constrained to move in a single axial direction by linear slides. X-stage 220 may in turn be connected with y-stage 222 that provides motion parallel to y-axis 224. X-stage 220 and y-stage 222 may be driven by separate linear motors, pneumatic actuators, hydraulic actuators, or the like. Additionally, clamp member 208 may be connected with clamp member drive 226 that rotates clamp member 208 about longitudinal axis 216. In an embodiment, clamp member drive 226 is a stepper motor, although clamp member drive 226 may instead include a motor having rotational movement controlled with feedback from a rotary encoder. Thus, clamp member 208 may be provided with at least three degrees of freedom, including bi-axial motion within a plane transverse to longitudinal axis 216 as well as rotational motion about longitudinal axis 216. Additional degrees of freedom may be achieved with more actuators.

Clamp member 208 and clamp hub 210 may further include numerous components that enable the slide clamping assembly to grip and support a plurality of microscope slides 212 separately from slide carrier 204. For example, spindle actuator 228 may actuate a locking mechanism of spindle 230 of clamp member 208 to longitudinally constrain clamp member 208 relative to clamp hub 210 and ensure that a microscope slide 212 remains firmly grasped by the slide clamping assembly 700. When locked together, clamp member 208 and clamp hub 210 may be moved in unison using motion sub-systems 114. The components and functions of the slide clamping assembly are described in further detail below.

In addition to the slide clamping assembly, microscope 104 may also include one or more cameras to provide for imaging of specimens on the various microscope slides 212 associated with slide carrier 204. In the embodiment described, microscope 104 includes a label camera, an overview camera, and a specimen camera. Each camera may be part of imaging sub-systems 106 and be positioned and configured to view different portions of the microscope slides 212 under different conditions. For example, label camera 250 may be supported on a structural frame of microscope 104 such that it captures a field of view of a label area on a microscope slide 212. As a result, label camera 250 may capture images or otherwise read data located in the label area. For example, images captured by label camera 250 may be processed by a vision system with optical character recognition capability to detect data included in the labels and enhance the speed of data entry, identification, and tracking of microscope slides 212. Data discernible from the label area may include patient identification information, slide 212 processing information, e.g., a stain type, and/or other information associated with the specimen.

In an alternative embodiment, identification of label information on a microscope slide 212 may include the use of an RFID reader in place of, or in addition to, label camera 250. For example, label camera 250 may include an Active Reader Passive Tag system to interrogate an RFID tag located on the label area of the microscope slide 212. Similarly, label camera 250 may include, in place of or in addition to optical recognition of label information, a barcode scanner to read a barcode on the label area that encodes identification or specimen data.

Imaging sub-systems 106 may also include overview camera 252 supported on a structural frame of microscope 104 and directed toward a specimen area of a microscope slide 212. Overview camera 252 may provide a low magnification view of a majority of the specimen area to allow a pathologist to quickly visualize a specimen and identify regions of interest within the specimen for further inspection. For example, overview camera 252 may be configured to capture an unmagnified image of all or a portion of the specimen area. In an embodiment, overview camera 252 captures several unmagnified images of specimen area portions, and those images are subsequently combined during image processing to provide a displayed image to a viewer that appears to be an unmagnified view of the entire specimen area.

Imaging sub-systems 106 may also include specimen camera 254 supported on a structural frame of microscope 104 and directed toward a specimen area of a microscope slide 212. Specimen camera 254 may provide a high magnification view of regions of interest of a specimen on a microscope slide 212. For example, specimen camera 254 may be used to capture highly focused regions of the specimen that allow a pathologist to provide a histological analysis of the specimen. Slides 212 may be formed from glass, and as is known in the art, specimens on slides 212 may be covered by glass or film during slide preparation. In an embodiment, specimen camera 254 includes one or more objective lenses that magnify the specimen area to allow specimen camera 254 to capture a magnified image. For example, a 2.5×, 10×, and or 20× objective lens may be used alone or in combination to magnify the specimen area. In addition to optical magnification, microscope 104 may be able to digitally magnify images captured by specimen camera 254 to provide even higher magnification. For example, in an embodiment, a specimen may be magnified 20× by an objective lens and the optically magnified image may be projected onto image sensor 108 and then digitally processed via computer 102 to further magnify the image and to display a digitally magnified image with an overall magnification of 40×.

Specimen camera 254 may be stabilized relative to slide clamping assembly to minimize relative movement that can degrade images captured under magnification. For example, specimen camera 254 and x-stage 220, which supports clamp member 208, may be connected to stabilization beam 255. Stabilization beam 255 may have comparatively higher mass to help dampen vibration. Furthermore, since both specimen camera 254 and x-stage 220 are fixed to stabilization beam 255 in an embodiment, any movement of stabilization beam 255 will transmit to both components. As a result, relative movement between specimen camera 254 and slides 212 attached to clamp member 208 may be minimized to contribute toward capturing a stable magnified image of specimen area 414.

Figure 3:
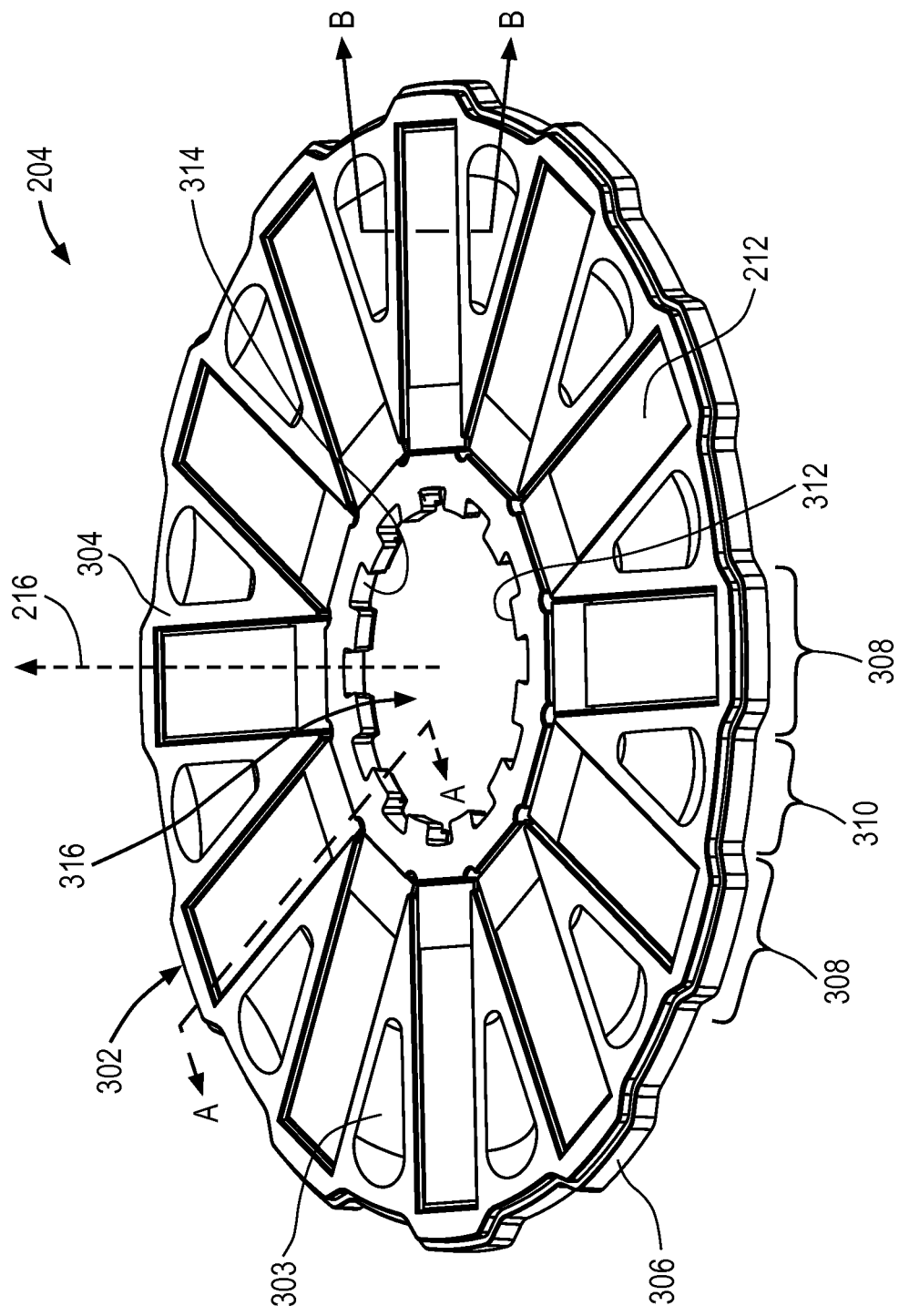
FIG. 3 is a perspective view of a microscope slide carrier in accordance with an embodiment of the invention.

Referring to FIG. 3, a perspective view of a microscope slide carrier is shown in accordance with an embodiment. Slide carrier 204 for holding a plurality of slides 212 may include body 302 having upper surface 304 perpendicular to longitudinal axis 216. Body 302 may be formed as a single object, e.g., as a monolithic plastic tray, or it may be formed in multiple parts, e.g., it may include an upper and lower portion that are snap fit, welded, or otherwise connected together. The singly formed body 302, or multiple constituent parts, may be molded, e.g., injection molded, cast, machined, or otherwise fabricated. Furthermore, the object or parts may be plastic, metallic, ceramic, etc. In an embodiment, body 302 may include outer wall 306 defining a thickness of slide carrier 204, as well as opening 316 centrally located in body 302. Opening 316 may be defined by inner wall 314 generally parallel to, and having the same thickness as, outer wall 306. Accordingly, in an embodiment, body 302 generally has the characteristics of an annular disk.

In an embodiment, body 302 includes one or more stacking groove 303. Stacking groove 303 may be a recess formed into upper surface 304. For example, stacking groove 303 may be a recess or pit configured to mesh with a stacking tongue or boss of an adjacent slide carrier 204. More particularly, slide carrier 204 may include a stacking tongue on a lower surface (not shown) that includes a negative form as compared to stacking groove 303. That is, the stacking tongue on a lower surface is shaped to mesh with stacking groove 303 within upper surface 304. Thus, slide carriers 204 may be stacked such that stacking groove 303 of one slide carrier 204 engages and meshes with a stacking tongue on a lower surface of an adjacent slide carrier 204. This meshing provides a stable grip between stacked slide carriers 204. Accordingly, slide carriers 204 are stackable to provide efficient and stable packing and transportation of a large number of slides 212 in an organized manner.

As discussed above, body 302 may include features to allow for slide carrier 204 to mesh with different components of microscope 104. For example, body 302 may include a perimeter contour with one or more wall protrusion 308 around the outer periphery of body 302. In an embodiment of more than one wall protrusion 308, wall protrusions 308 may be separated by one or more wall recesses 310. Thus, wall protrusions 308 and wall recesses 310 in combination create an undulating surface around the perimeter of body 302. In essence, wall protrusions 308 provide one or more tooth extending radially from an outer wall of body 302. In an embodiment, this undulating surface conforms with an edge profile of a recess in shelf 202 of microscope 104 such that slide carrier 204 may be loaded into the recess and the edge profile may engage the outer wall 306 of slide carrier 204 to prevent slide carrier 204 from rotating within the recess. Thus, wall protrusions 308 provide teeth that mesh with teeth provided by a recess in shelf 202.

Figure 4:
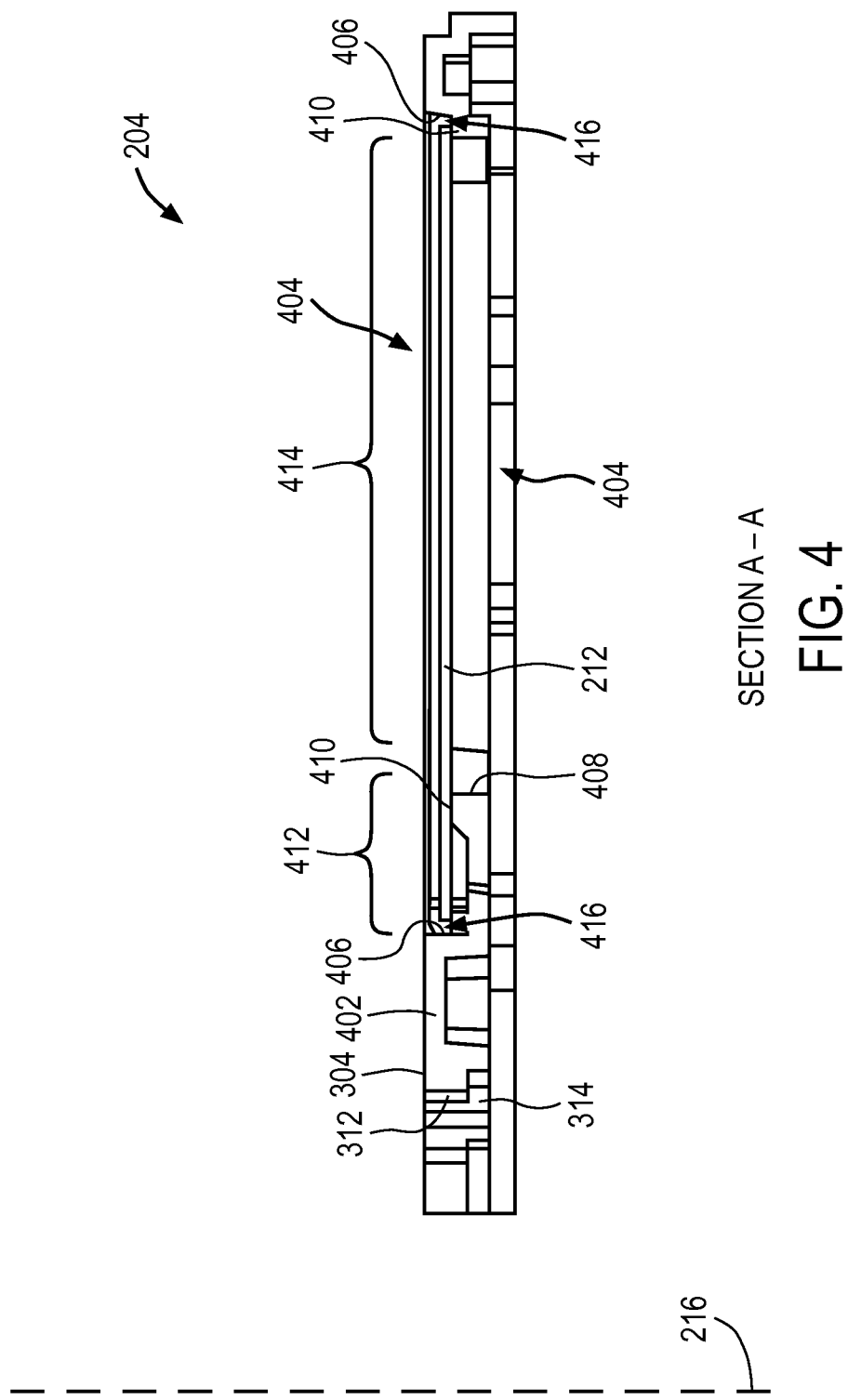
FIG. 4 is a cross-section view, taken about line A-A of FIG. 3, of a slide receptacle and carrier tooth region of a microscope slide carrier in accordance with an embodiment of the invention.

Referring to FIG. 4, a cross-section view, taken about line A-A of FIG. 3, of a slide receptacle and carrier tooth region of a microscope slide carrier is shown in accordance with an embodiment. In an embodiment, body 302 includes carrier tooth 312 protruding inward from inner wall 314. For example, carrier tooth 312 may extend in a generally radial direction from central hub 402 portion of body 302 toward longitudinal axis 216. Carrier tooth 312 may be configured to mesh with a tooth of clamp hub 210, as described further below.

In an embodiment, body 302 includes one or more slide receptacles formed in body 302 for holding microscope slides 212. Slide receptacle 404 may include an outer profile 406 at a furthermost perimeter, as well as inner profile 408 at an innermost perimeter. More specifically, outer profile 406 may be defined by a recess in upper surface 304 that only extends partially through body 302, while inner profile 408 may be defined by a hole in upper surface 304 that extends fully through body 302. Since outer profile 406 and inner profile 408 may not be the same profile, in an embodiment, the mismatch between outer profile 406 and inner profile 408 provides carrier support 410. Carrier support 410 may create a shelf or lip within the perimeter of outer profile 406 such that slide 212 may be inserted within slide receptacle 404 and rest or be supported on carrier support 410. For example, slide 212 may be placed on carrier support 410 with label area 412 radially inward from specimen area 414 of the slide 212. In an embodiment, outer profile 406 of slide receptacle 404 is larger than an outer perimeter of slide 212 such that gap 416 is provided or defined between the edge of slide 212 and outer profile 406 and/or inner profile 408. As a result of gap 416, slide 212 may be loosely supported within slide receptacle 404. For example, gap 416 may provide a space of about 0.5 to 2 mm around the perimeter of slide 212, between slide 212 and outer profile 406 and/or inner profile 408. Accordingly, slide 212 may be loaded and unloaded quickly into the oversized slide receptacle 404 without catching or interfering with a ledge of slide receptacle 404. Furthermore, slide carrier 204 may be manufactured with relatively low precision processes with less risk of being undersized for slides 212.

Although slide 212 may be loosely supported on a lip or other rest, such as carrier support 410, additional mechanisms for supporting and/or retaining slide 212 in slide receptacle 404 may be used. For example, slide 212 may have a friction fit or a sliding fit within slide receptacle 404, allowing for slide 212 to be easily inserted and removed from slide receptacle 404. A smaller gap 416 between the edge of slide 212 and outer profile 406 may be used in such embodiments. In an embodiment, alternative carrier support 410 configurations may be used, such as spring members, cushion pads, or other rests that can support and/or retain slide 212 within slide receptacle 404. Carrier support 410 is not required to extend around the entire perimeter of slide receptacle. For example, one or more notches, protrusions, pegs, etc. may extend from a slide receptacle 404 wall such that slide 212 placed within slide receptacle 404 may be supported and/or retained therein. An example of another retention mechanism includes a leaf spring mechanism or another pressure-applying mechanism that may apply a lateral load to slide 212 while it is retained within slide receptacle 404. As a result of the lateral load, slide 212 may be secured within slide receptacle under a slight pressure that does not prevent slide 212 from later being lifted out of slide receptacle. Thus, it will be appreciated that numerous variations of slide receptacle 404 and/or means for supporting and retaining slide 212 within slide carrier 204 are contemplated to be within the scope of this disclosure.

Figure 5:
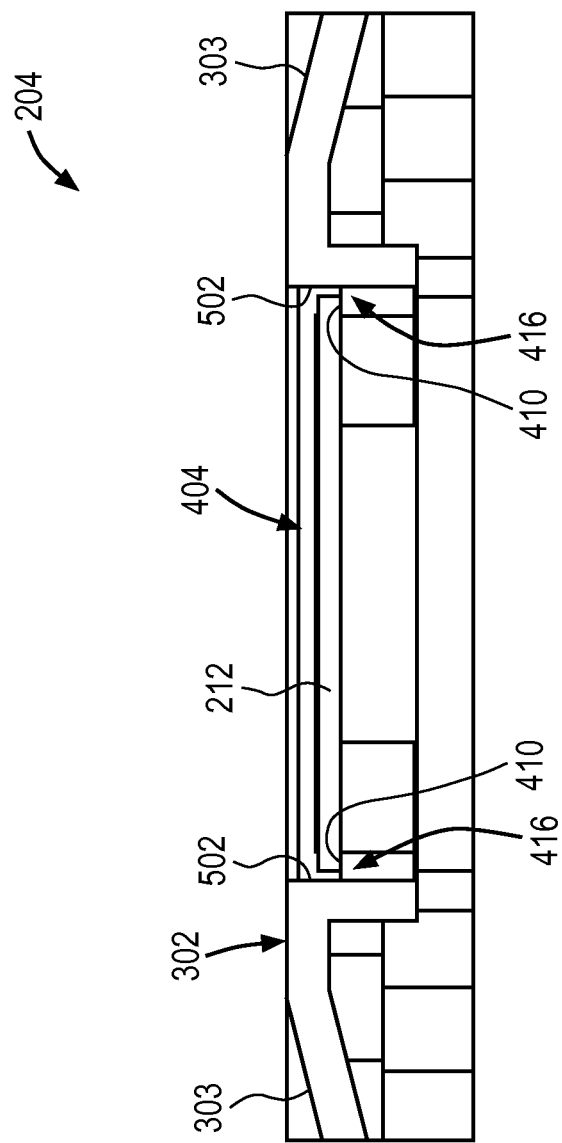
FIG. 5 is a cross-section view, taken about line B-B of FIG. 3, of a slide receptacle region of a microscope slide carrier in accordance with an embodiment of the invention.

Referring to FIG. 5, a cross-section view, taken about line B-B of FIG. 3, of a slide receptacle region of a microscope slide carrier is shown in accordance with an embodiment. In an embodiment, slide receptacle 404 is formed in body 302 laterally between stacking grooves 303. Slide 212 may be inserted into slide receptacles 404, and as described above, gap 416 may surround slide 212 such that slide 212 rests loosely on support between sidewalls 502 of slide receptacle 404.

Figure 6:
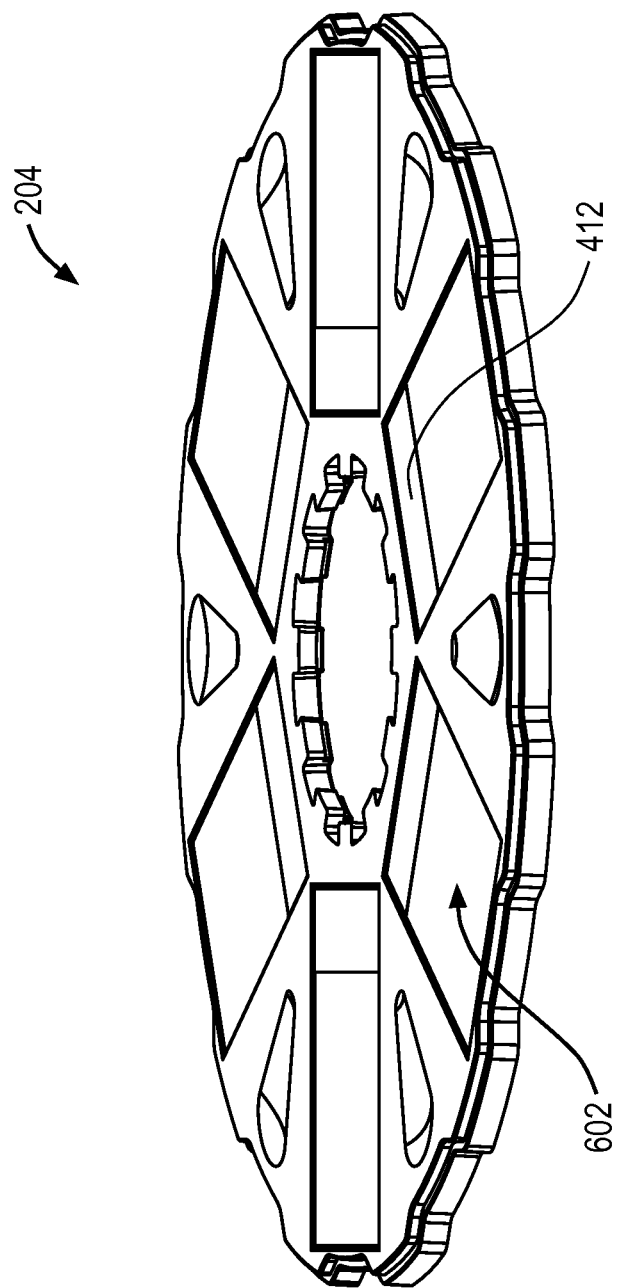
FIG. 6 is a perspective view of a microscope slide carrier in accordance with an alternative embodiment of the invention.

Referring to FIG. 6, a perspective view of a microscope slide carrier is shown in accordance with an alternative embodiment. Slide carrier 204 may be modified to hold a range of slide quantities and slide sizes. For example, slide carrier 204 may be configured to receive one or more megaslide 602 that has outer dimensions that are larger than slides 212 shown in FIG. 3. In an embodiment, conventional slides 212 in FIG. 3 include outer dimensions of about 1-inch wide by 3-inches long, while megaslides 602 in FIG. 6 include outer dimensions of about 3-inches wide by 6-inches long. Thus, slide carrier 204 of the same size may be configured to hold about six megaslides 602, as opposed to holding about twelve conventional slides 212. These quantities are not restrictive however, and carrier slide 212 may be modified to hold any number of slides of any size. In an embodiment, slide carriers 204 holding differently sized slides may be examined consecutively in microscope 104, and microscope 104 may recognize the slide configuration and size according to data provided anywhere on the slide, e.g., on label area 412, or imprinted on upper surface 304 of slide carrier 204.

Slide carrier 204 may include index imprints to identify each slide receptacle 404 of slide carrier 204. In an embodiment, an index imprint includes a number stamped on slide carrier 204 surface near the associated slide receptacle 404. For example, in a case in which slide carrier 204 includes twelve slide receptacles 404, index imprints may vary between 1 and 12 around the circumference of the slide carrier 204. Thus, a first slide receptacle 404 can be identified by an adjacently imprinted numeral one, and so on. Accordingly, slide receptacles 404 may be identified, either manually or automatically, for various reasons. For example, identification of the numeral one may be automatically identified by a vision system to allow the first slide receptacle 404 to be rotated into an initial viewing position, regardless of how a user loaded slide carrier 204 onto shelf 202. In another embodiment, index imprints may indicate to a technician an ordering for loading slides 212 into slide receptacles 404, e.g., a first slide 212 may be placed in a first slide receptacle 404, and so on.

Figure 7:
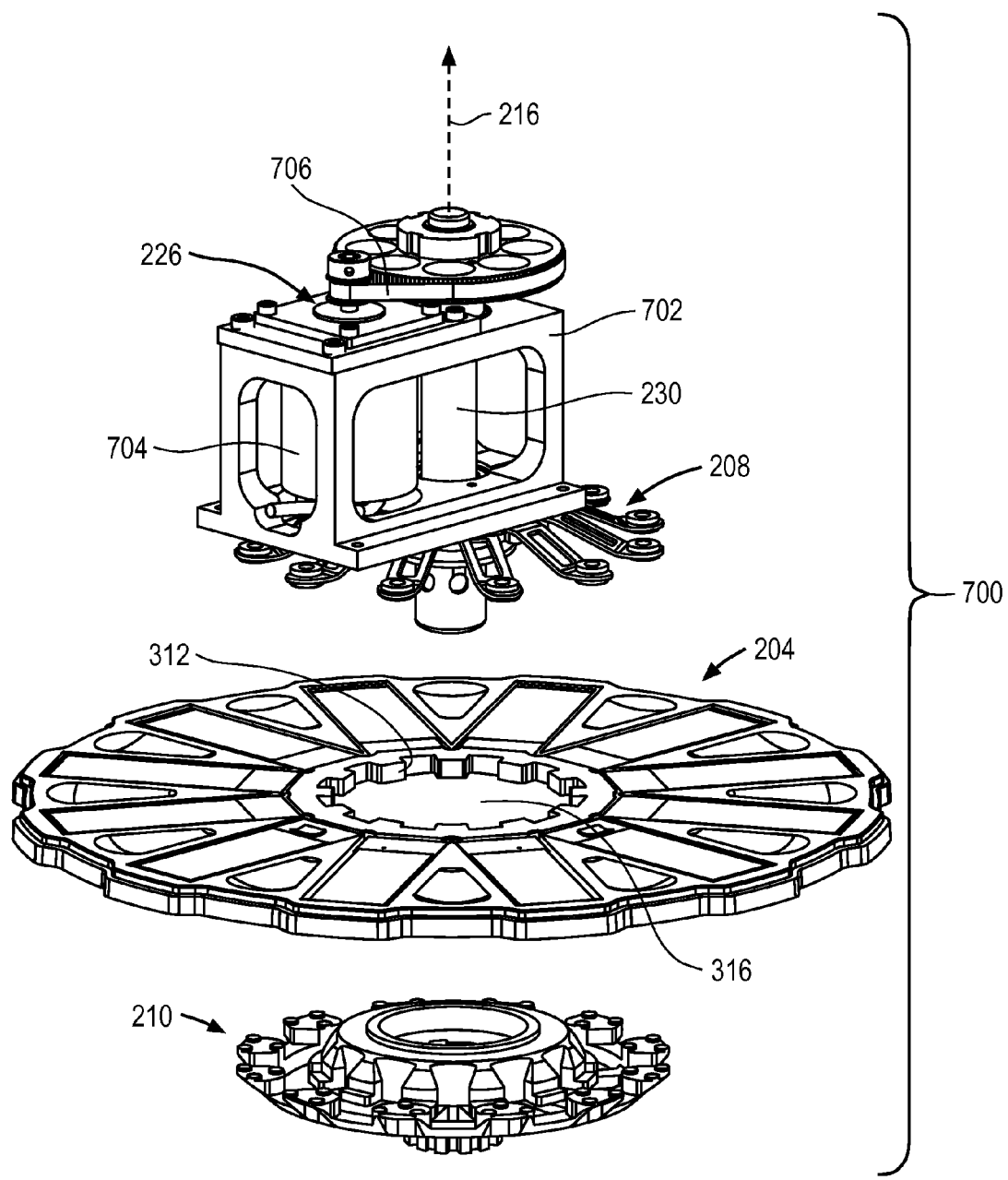
FIG. 7 is a perspective view of a slide clamping assembly of a microscope exploded along a longitudinal axis in accordance with an embodiment of the invention.

Referring to FIG. 7, a perspective view of a slide clamping assembly of a microscope exploded along a longitudinal axis is shown in accordance with an embodiment. In an embodiment, slide clamping assembly 700 of microscope 104 includes clamp member 208 and clamp hub 210 arranged along longitudinal axis 216. Clamp member 208 may include spindle 230 that is rotationally constrained within clamp member frame 702. Clamp member frame 702 may be connected with x-stage 220 and y-stage 222 of clamp member motion sub-system 120 to provide for movement of clamp member 208 within a plane transverse to longitudinal axis 216. In an embodiment, clamp member frame 702 also supports clamp member drive 226 of clamp member motion sub-system 120 to rotationally drive spindle 230. More specifically, clamp member drive 226 may include clamp member motor 704 connected with spindle 230 by drive belt 706 that transmits rotational motion from a motor shaft of clamp member motor 704 to spindle 230. Clamp hub 210 may be radially aligned with clamp member 208 and may be moved in numerous directions by clamp hub motion sub-system 118, as described above. Furthermore, in a configuration, slide carrier 204 may be radially aligned with clamp member 208 and clamp hub 210 such that longitudinal axis 216 passes through spindle 230, opening 316, and clamp hub 210. The radially aligned configuration illustrated in FIG. 7 may correspond, for example, to a moment in which slide carrier 204 has been moved into microscope 104 between clamp member 208 and clamp hub 210 by shelf 202, but prior to clamp hub 210 being raised upward to engage carrier tooth 312 with a tooth of clamp hub 210 and/or prior to clamping slides 212 between clamp member 208 and clamp hub 210.

Figure 8:
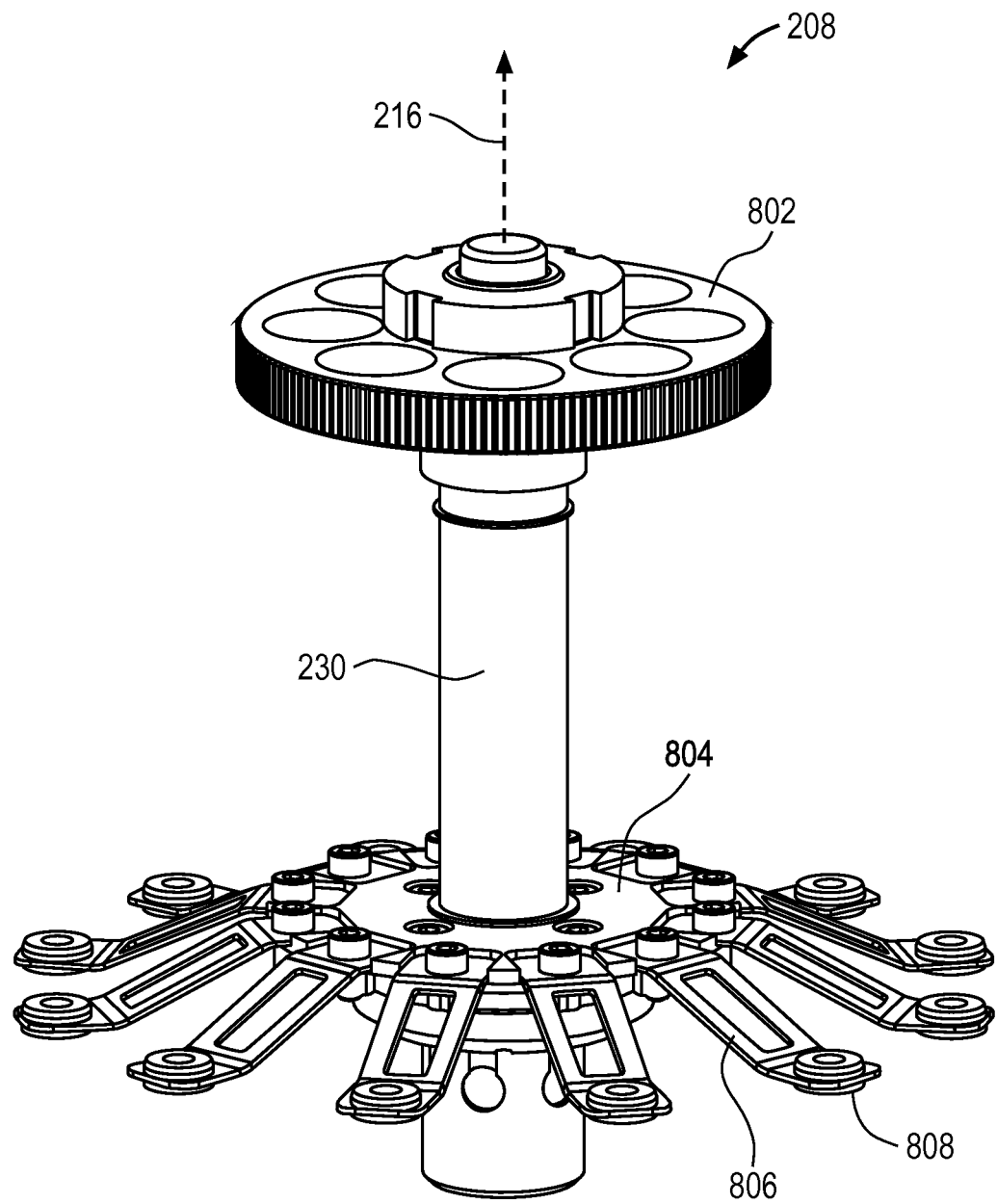
FIG. 8 is a perspective view of a clamp member of a microscope in accordance with an embodiment of the invention.

Referring to FIG. 8, a perspective view of a clamp member of a microscope is shown in accordance with an embodiment. In this embodiment, clamp member 208 includes spindle 230 connected with drive gear 802 such that drive belt 706 meshes with drive gear 802 to impart rotational motion to spindle 230. In an embodiment, clamp plate 804 is rigidly connected with spindle 230 such that clamp plate 804 moves with spindle 230. Clamp member 208 may include one or more finger 806 extending in a generally radial direction away from longitudinal axis 216. More specifically, each finger 806 may be connected to clamp plate 804 at a first end and cantilever away from clamp plate 804 toward a second end radially outward from the first end. However, fingers 806 need not extend purely radially. For example, fingers 806 may extend along a curvilinear path from the first end to the second end. Furthermore, clamp nub 808 may be located near the second end of finger 806. For example, clamp nub 808 may be a grommet that is placed through a longitudinal hole near the second end of finger 806. In an embodiment, clamp nub 808 is formed from a material that is softer than finger 806 material. For example, clamp nub 808 may be an elastomer, e.g., rubber, while finger 806 may be formed from a metal, e.g., steel or aluminum.

Figure 9:
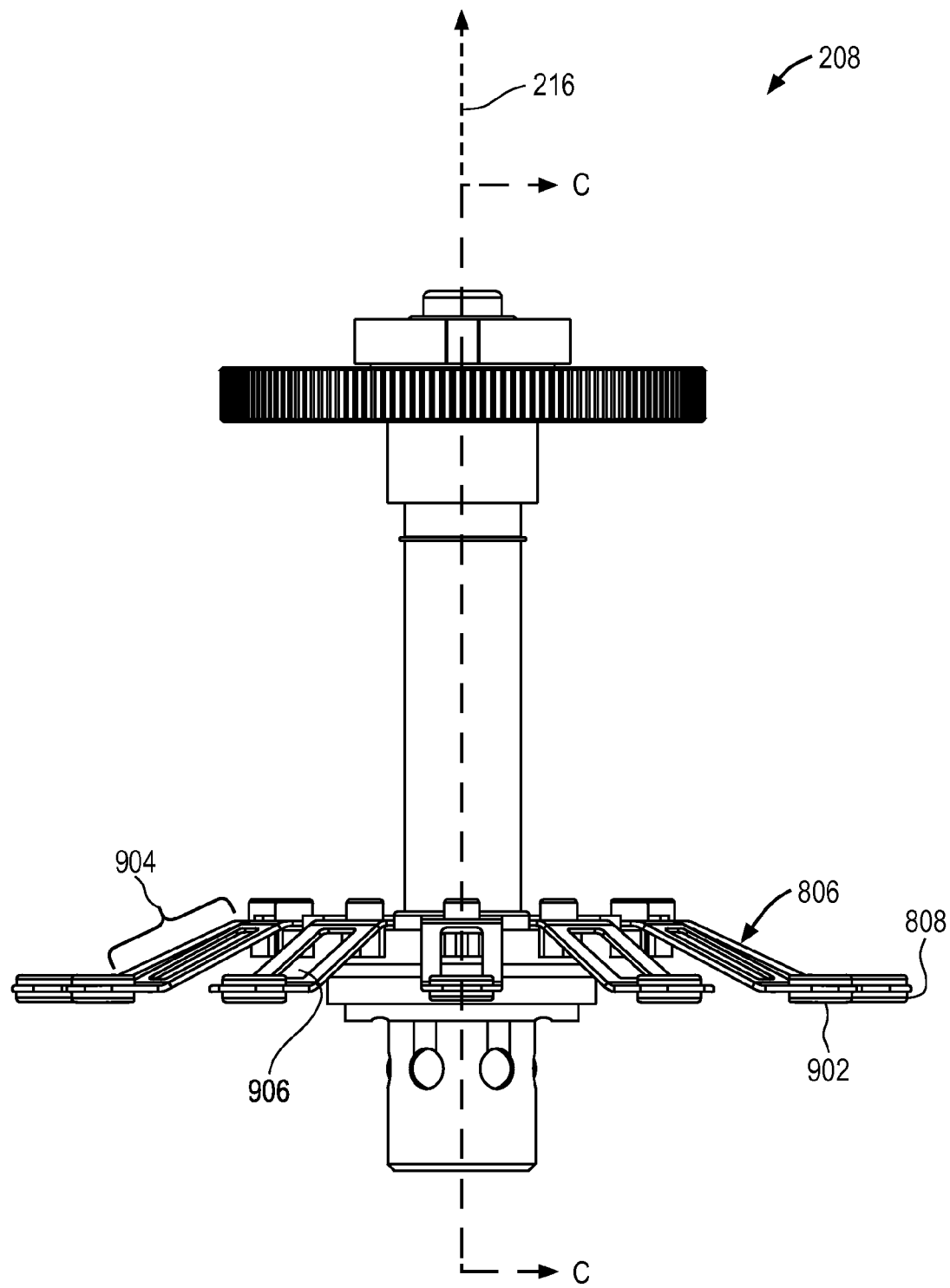
FIG. 9 is a side view of a clamp member of a microscope in accordance with an embodiment of the invention.

Referring to FIG. 9, a side view of a clamp member of a microscope is shown in accordance with an embodiment. Clamp member 208 may include clamp surface 902 on a lower portion of clamp nub 808. Clamp surface 902 may be generally perpendicular, i.e., transverse, to longitudinal axis 216 passing through spindle 230. Accordingly, when slide carrier 204 loosely holding slides 212 is raised toward clamp member 208, clamp surface 902 may press against an upper surface of the slide, such as label area 412 of slide 212.

In an embodiment, finger 806 includes spring portion 904 along its radially extending length. For example, spring portion 904 may be a region of finger 806 that extends radially, but also in a longitudinal direction, i.e., a slanted direction. Spring portion 904 may include a cross-section area less than a cross-sectional area of other portions of finger 806. For example, spring portion 904 may include finger slot 906 formed through the thickness of finger 806 to reduce the cross-sectional area and therefore the stiffness of finger 806 in the slotted region. Alternatively, spring portion 904 may be thinner than other portions of finger 806 to increase flexibility of finger 806 in that region. Accordingly, spring portion 904 may provide flexibility to finger 806 such that finger 806 is able to resiliently deflect when a slide 212 in slide carrier 204 is clamped between clamp surface 902 and clamp hub 210.

Figure 10:
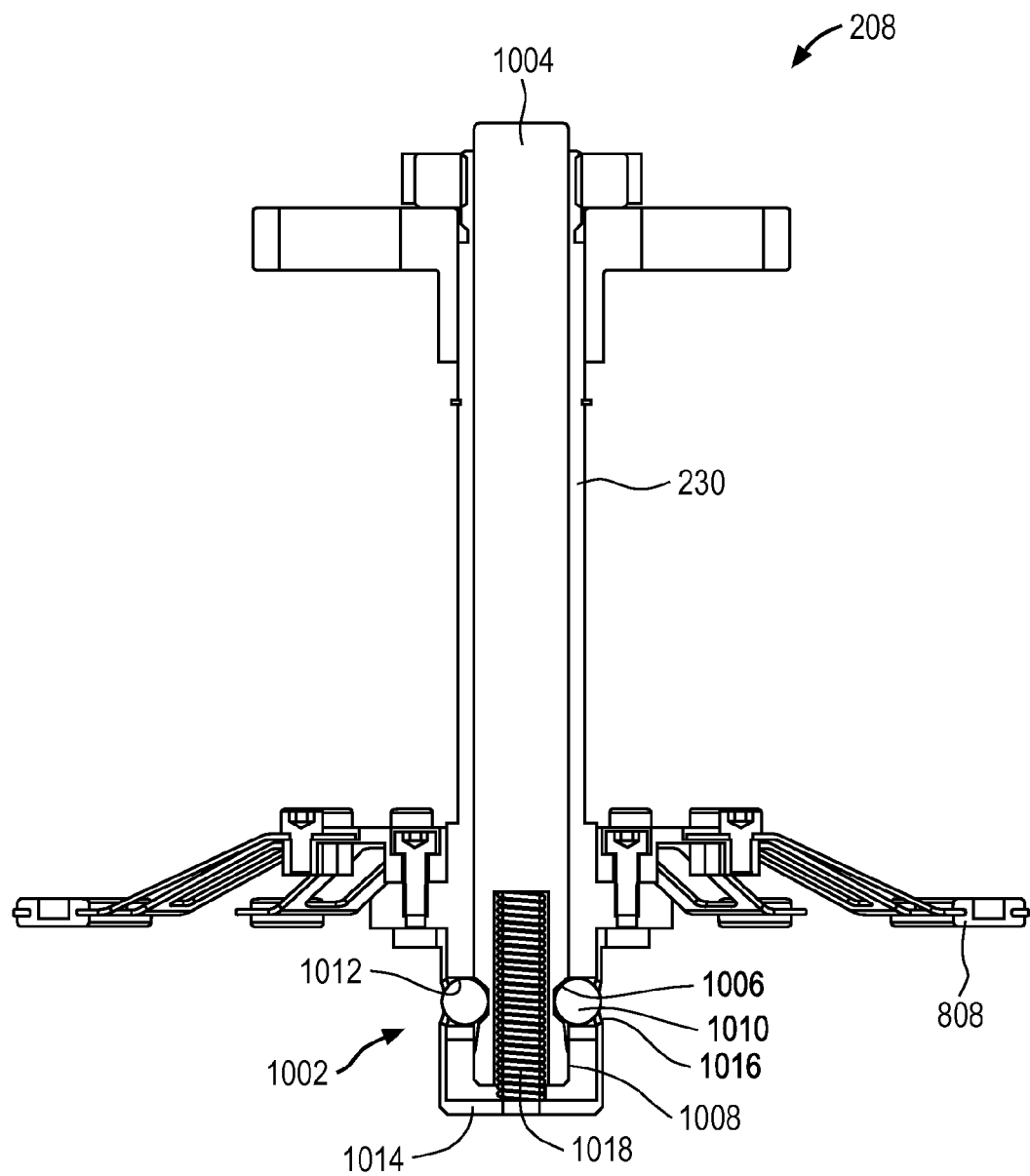
FIG. 10 is a cross-section view, taken about line C-C of FIG. 9, of a clamp member of a microscope in accordance with an embodiment of the invention.

Referring to FIG. 10, a cross-section view, taken about line C-C of FIG. 9, of a clamp member of a microscope is shown in accordance with an embodiment. In this embodiment, clamp member 208 includes locking mechanism 1002 that is controllably engaged and disengaged by actuating shaft 1004. More particularly, shaft 1004 may be slidably disposed within spindle 230. Thus, at least a portion of spindle 230 may be tubular to receive shaft 1004. Shaft 1004 may include shaft outer surface 1008 and shaft groove 1006 defined in a portion of shaft 1004, such as around a perimeter of the shaft located near a lower portion of shaft 1004 in a vicinity of one or more lock ball 1010. In an embodiment, shaft groove 1006 has a diameter less than a diameter of shaft 1004 allowing lock ball 1010 to be retained within spindle slot 1012 such that lock ball 1010 may move laterally depending upon the relative position between shaft 1004 and spindle 230. For example, when shaft 1004 is in a downward position with shaft groove 1006 transversely aligned with spindle slot 1012, lock ball 1010 may tend laterally inward to rest within shaft groove 1006. By contrast, when shaft 1004 is in an upward position with shaft groove 1006 transversely misaligned with spindle slot 1012, shaft outer surface 1008 may press lock ball 1010 laterally outward through spindle slot 1012. Optionally, spindle 230 may be constructed in two parts, having spindle cap 1014 connected to spindle 230. In such a case, spindle cap 1014 may include spindle cap slot 1016 that, like spindle slot 1012, may retain lock ball 1010 and provide a slot for lock ball 1010 to extend or retract laterally depending upon alignment between shaft 1004 and spindle 230.

In an embodiment, shaft spring 1018 may bias shaft 1004 in an upward, i.e., locked, position. In the locked position, lock ball 1010 extends outward to engage a portion of clamp hub 210 and thereby retain clamp hub 210 in a fixed position relative to spindle 230. When slide 212 is positioned between clamp nub 808 and clamp hub 210 in this locked position, a clamping pressure may be placed on the slide 212. Thus, with the locking mechanism 1002 locked, slides 212 may be clamped and retained in a fixed position relative to clamp member 208.

In an embodiment, a downward force may be applied in a longitudinal direction to shaft 1004 by an external actuator. For example, spindle actuator 228, e.g., a hydraulic, pneumatic, or electrically-driven linear actuator, may press downward on shaft 1004 to overcome shaft spring 1018 biasing load and to align shaft groove 1006 with spindle slot 1012. Accordingly, locking mechanism 1002 transitions toward an unlocked position in which lock ball 1010 may retract laterally inward and release clamp hub 210. Upon unlocking, clamp hub 210 may fall downward and away from clamp nub 808, thereby releasing slides 212 that may have been clamped therebetween.

Locking mechanism 1002 may be locked and unlocked in other manners to retain clamp hub 210 relative to clamp member 208 and to grip a slide 212 therebetween. For example, in an embodiment, locking mechanism 1002 may include an electromagnet integrated within spindle 230 to direct an electromagnetic force along longitudinal axis 216. Accordingly, by constructing clamp hub 210 of a magnetic material, such as a paramagnetic or ferromagnetic material, the electromagnet may be energized to attract clamp hub 210 toward clamp nub 808 and clamp slide 212 therebetween. Similarly, the electromagnet may be de-energized to release clamp hub 210 and thereby unclamp slide 212. It will be appreciated that various other locking mechanisms 1002 may be devised to controllably connect clamp member 208 with clamp hub 210 within the scope of this description, and thus, the locking mechanism 1002 examples provided above are illustrative but not limiting.

Figure 11:
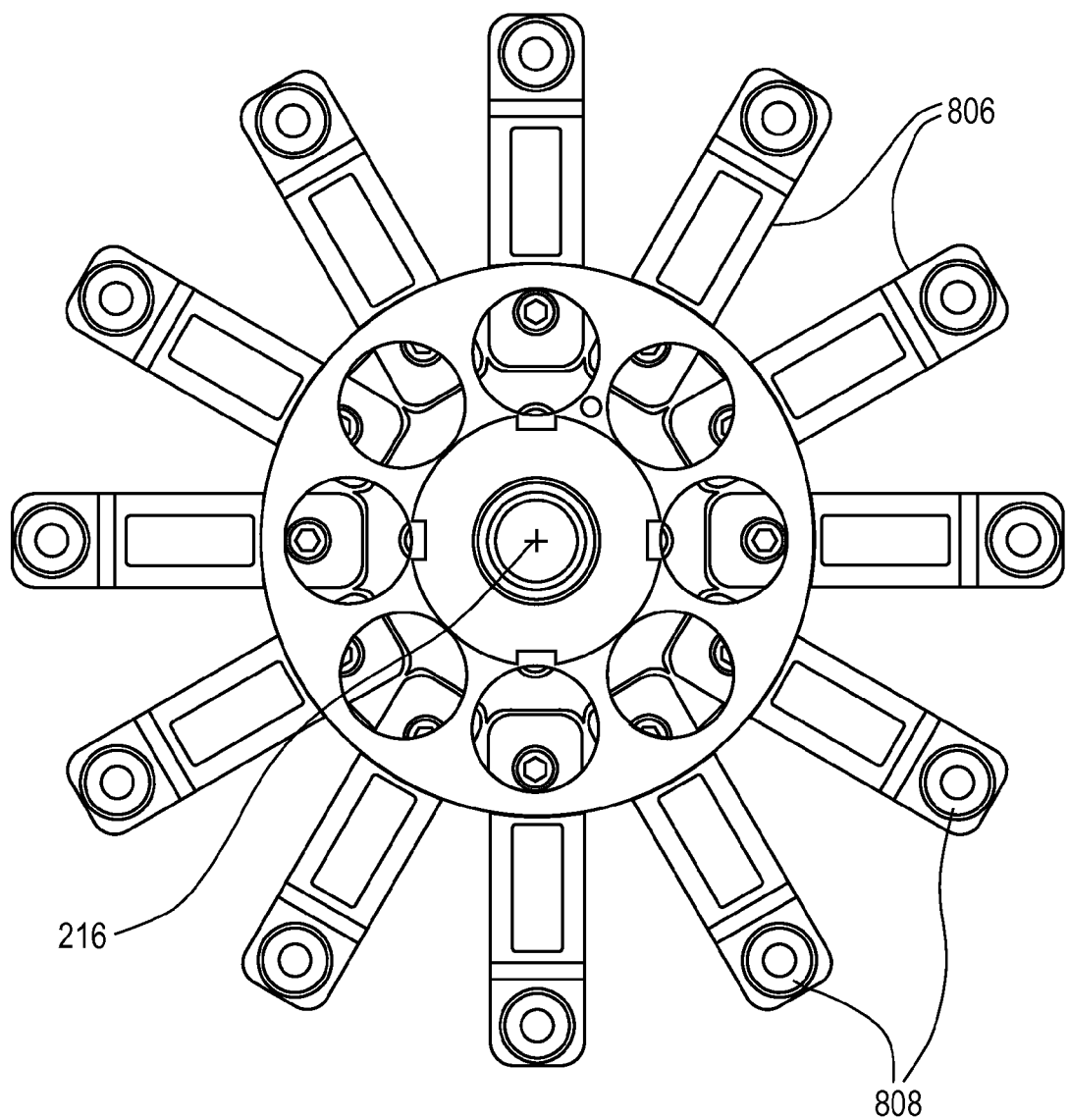
FIG. 11 is a top view of a clamp member of a microscope in accordance with an embodiment of the invention.

Referring to FIG. 11, a top view of a clamp member of a microscope is shown in accordance with an embodiment. In an embodiment, plurality of fingers 806 extend radially away from longitudinal axis 216 such that clamp nubs 808 are arranged circumferentially about longitudinal axis 216. As shown, clamp nubs 808 may be spaced at the same radial distance from longitudinal axis 216, however, circumferential arrangement of elements within this description does not necessarily require that the elements are evenly spaced along a circle, but rather that the elements are all radially spaced apart from longitudinal axis 216 and arranged in some pattern that describes an angle about longitudinal axis 216.

Figure 12:
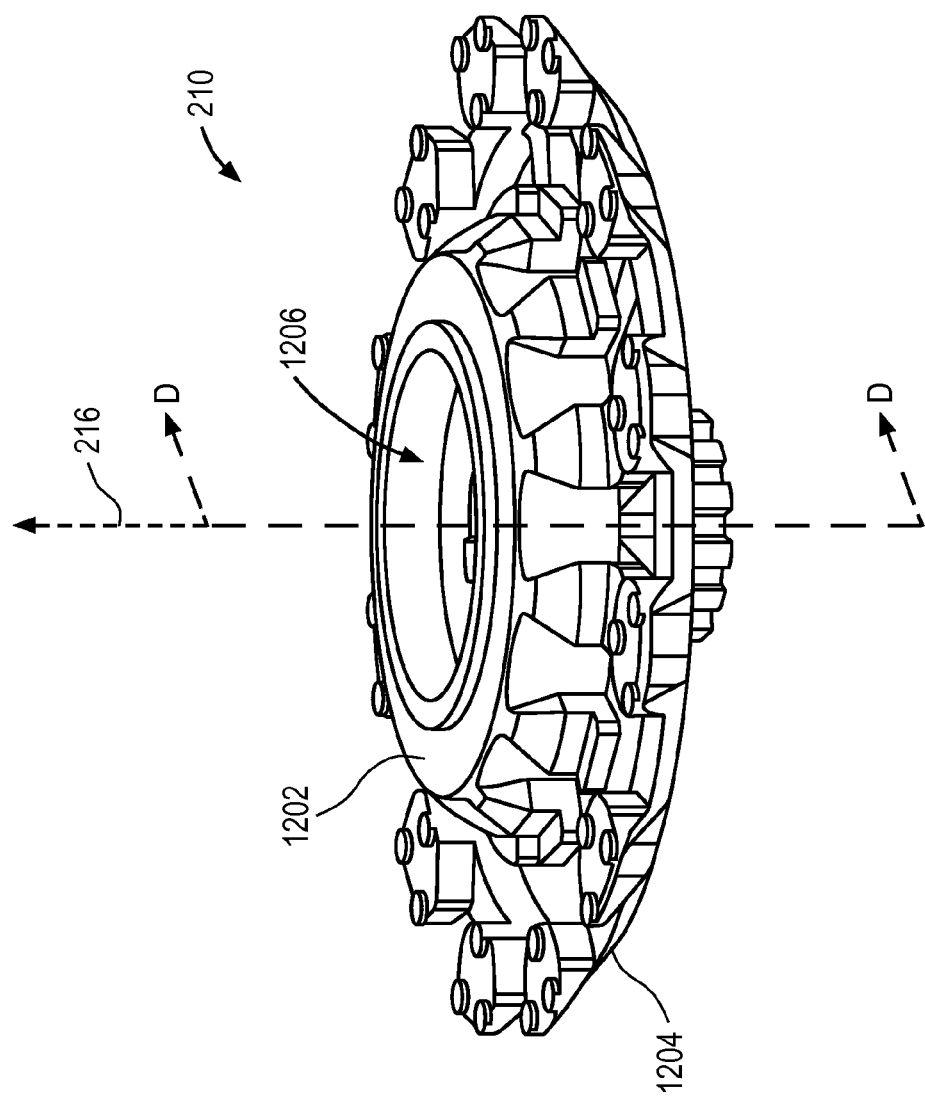
FIG. 12 is a perspective view of a clamp hub of a microscope in accordance with an embodiment of the invention.

Referring to FIG. 12, a perspective view of a clamp hub of a microscope is shown in accordance with an embodiment. Clamp hub 210 may include several components, including slide carrier receiver 1202 and slide seating plate 1204. Slide carrier receiver 1202 and slide seating plate 1204 may be radially aligned along longitudinal axis 216. Furthermore, in an embodiment, slide carrier receiver 1202 and slide seating plate 1204 each constitute a body defining an opening about longitudinal axis 216 (openings 1206) that permit spindle 230 of clamp member 208 to engage clamp hub 210 and therefore maintain radial alignment between clamp member 208 and clamp hub 210.

Figure 13:
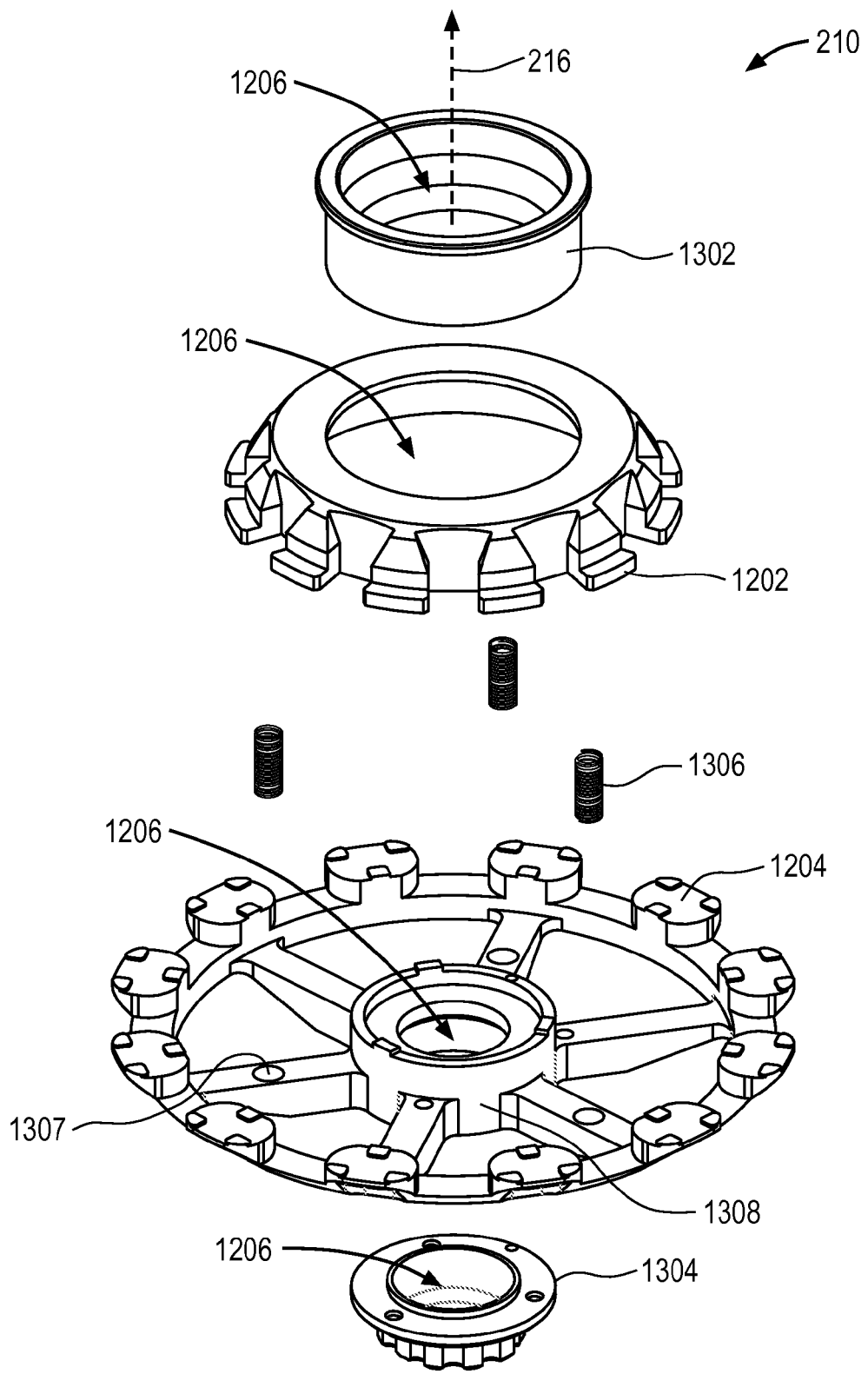
FIG. 13 is a perspective view of a clamp hub of a microscope exploded along a longitudinal axis in accordance with an embodiment of the invention.

Referring to FIG. 13, a perspective view of a clamp hub of a microscope exploded along a longitudinal axis is shown in accordance with an embodiment. In an embodiment, clamp hub 210 includes bushing 1302 and end cap 1304 in addition to slide carrier receiver 1202 and slide seating plate 1204. Both bushing 1302 and end cap 1304 may be fastened to slide seating plate 1204 using various mechanical fasteners. Furthermore, bushing 1302 may be sized to insert through the central opening 1206 of slide carrier receiver 1202 in a sliding fit. Accordingly, when fully assembled, clamp hub 210 may include slide carrier receiver 1202 that is constrained in radial alignment with slide seating plate 1204. However, in an embodiment, slide carrier receiver 1202 slides over an outer perimeter of bushing 1302, which is fixed to slide seating plate 1204, and therefore slide carrier receiver 1202 may move longitudinally relative to slide seating plate 1204.

In an embodiment, a biasing element, such as one or more spring 1306 may be provided in clamp hub 210 to bias slide carrier receiver 1202 away from slide seating plate 1204. For example, one or more spring 1306 may be located and connected between slide carrier receiver 1202 and slide seating plate 1204 to bias those components apart longitudinally. Spring 1306 may be a compression spring, and each end of spring 1306 may be located in respective counterbore 1307 formed in slide carrier receiver 1202 and slide seating plate 1204. Mechanical preload in spring 1306 may be predefined or adjustable based on the length of bushing 1302, which permits slide carrier receiver 1202 to be pushed away from slide seating plate 1204 to a fixed distance. In an alternative embodiment, rather than incorporating several springs 1306 arranged circumferentially about longitudinal axis 216, a single compression spring may be used with a minor diameter greater than central plate hub 1308 of slide seating plate 1204. Different spring 1306 configurations may be evident to one skilled in the art, such as incorporating a tension spring between bushing 1302 and slide carrier receiver 1202 to pull the latter component away from slide seating plate 1204.

Figure 14:
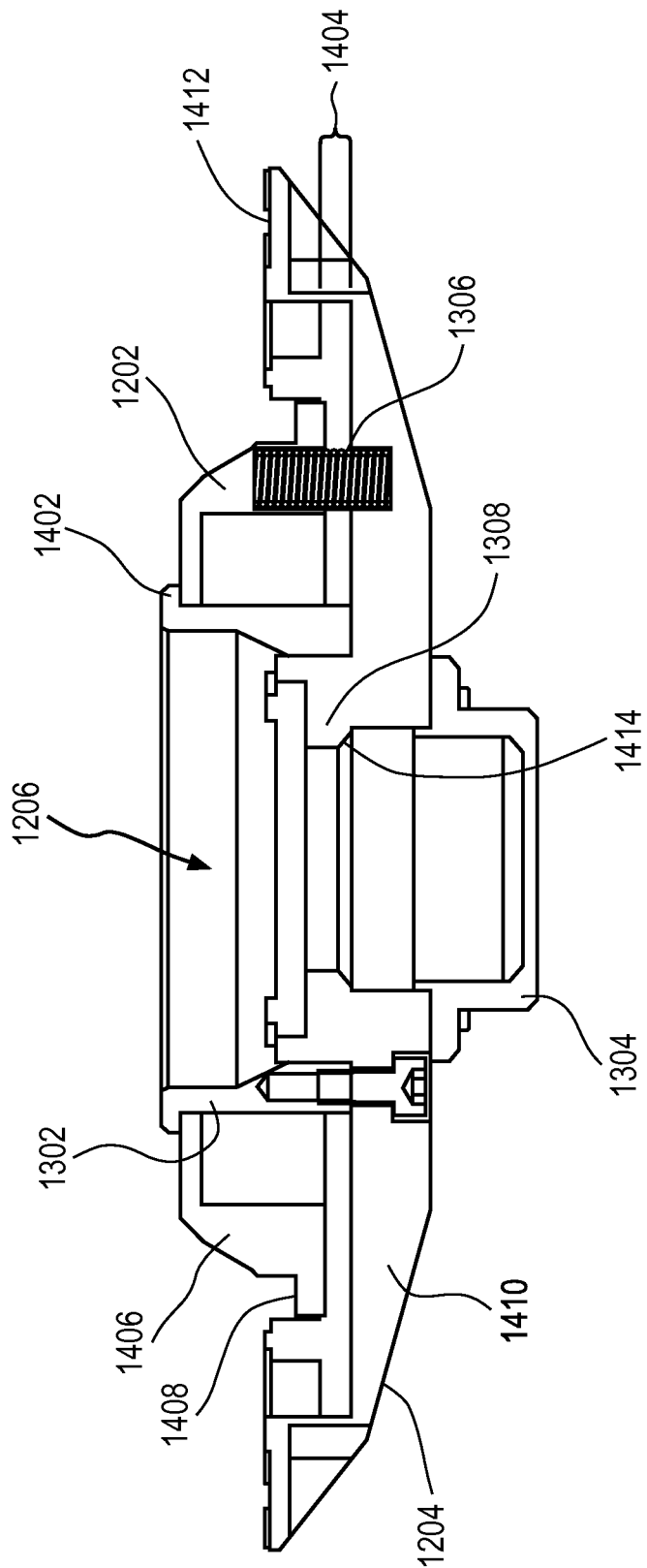
FIG. 14 is a cross-section view, taken about line D-D of FIG. 12, of a clamp hub of a microscope in accordance with an embodiment of the invention.

Referring to FIG. 14, a cross-section view, taken about line D-D of FIG. 12, of a clamp hub of a microscope is shown in accordance with an embodiment. In an embodiment, slide carrier receiver 1202 sliding over bushing 1302 is constrained longitudinally by bushing lip 1402. In other words, as spring 1306 biases slide carrier receiver 1202 away from slide seating plate 1204, bias gap 1404 may form between slide carrier receiver 1202 and slide seating plate 1204. However, bias gap 1404 may be limited to a maximum dimension controlled by placement of bushing lip 1402. Bias gap 1404 may also vary based on external loading of clamp hub 210. In an embodiment, slide seating plate 1204 includes lock chamfer 1414 to receive one or more lock ball 1010 of locking mechanism 1002 of clamp member 208. Thus, when spindle 230 is inserted through central opening 1206 of clamp hub 210, locking mechanism 1002 may be actuated to engage lock ball 1010 with lock chamfer 1414 and thus prevent spindle 230 from being pulled out of the central opening 1206. That is, lock ball 1010 may be engaged with lock chamfer 1414 to fix clamp member 208 to clamp hub 210 in an axial direction.

Figure 15A:
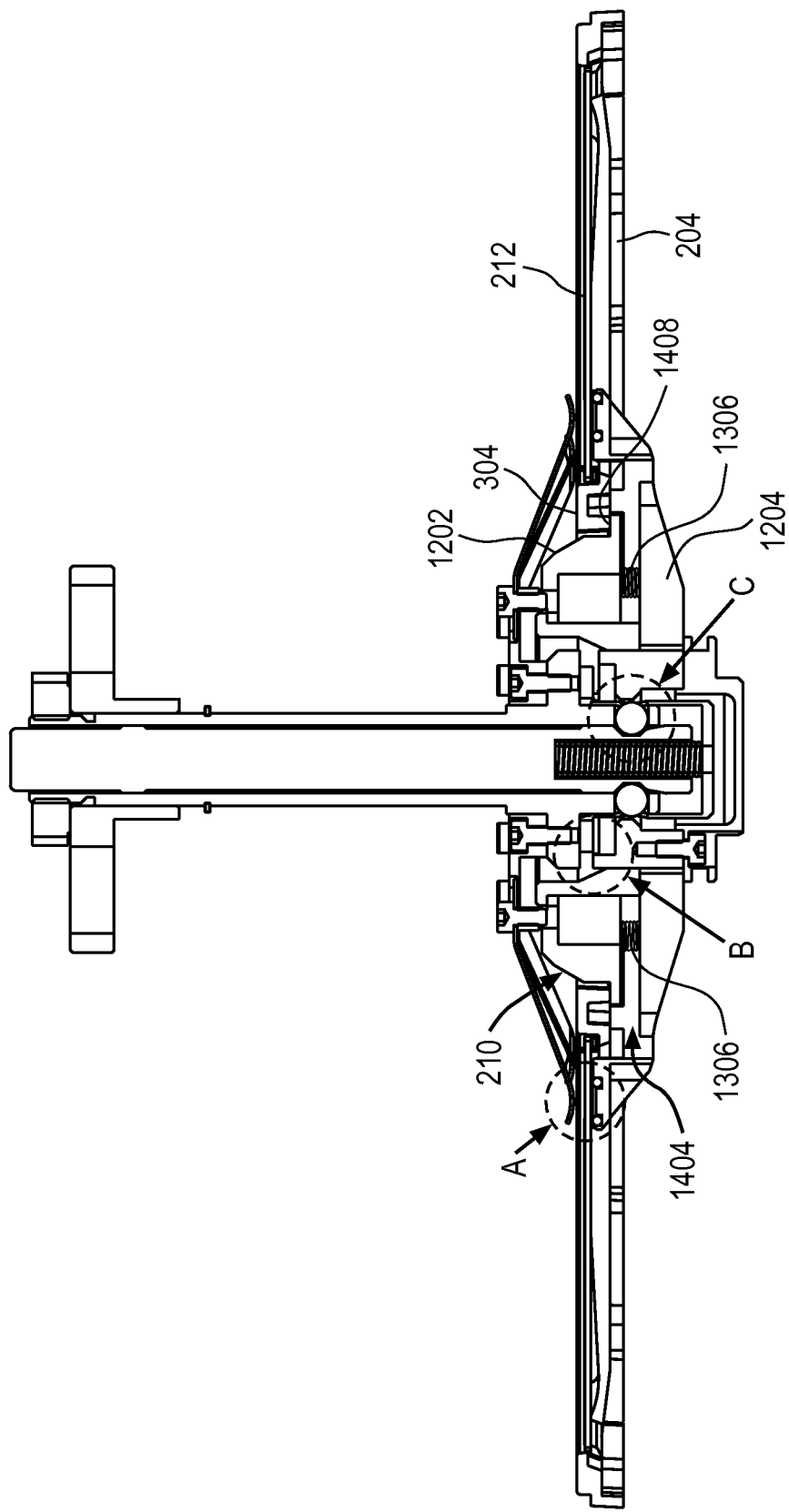
FIG. 15A is a cross-section view of a slide carrier resting on a clamp hub of a microscope in accordance with an embodiment of the invention.

Referring to FIG. 15A, a cross-section view of a slide carrier resting on a clamp hub of a microscope is shown in accordance with an embodiment. In an embodiment, spring 1306 is tuned to deflect only under a given load. For example, in a first configuration of clamp hub 210, spring 1306 may support the weight of slide carrier 204 fully loaded with slides 212, without deflecting. Slide carrier receiver 1202 may be configured to receive slide carrier 204. For example, central opening 316 of slide carrier 204 may fit around an outer profile of slide carrier receiver 1202. More particularly, a plurality of receiver teeth on slide carrier receiver 1202 may engage and/or mesh with a plurality of carrier teeth 312 on slide carrier 204. Slide carrier 204 may move further toward slide seating plate 1204 as the teeth mesh, until receiver support 1408 engages a lower surface of slide carrier 204 opposite from upper surface 304 of slide carrier body 302. Accordingly, slide carrier 204 may be fully supported by slide carrier receiver 1202 with spring 1306 either not deflecting or only marginally deflecting to allow slides 212 to remain supported by slide carrier support 410. Thus, in a first configuration, slide carrier 204 may be supported by clamp hub 210 without separating the slides 212 from slide carrier 204.

Figure 15B:
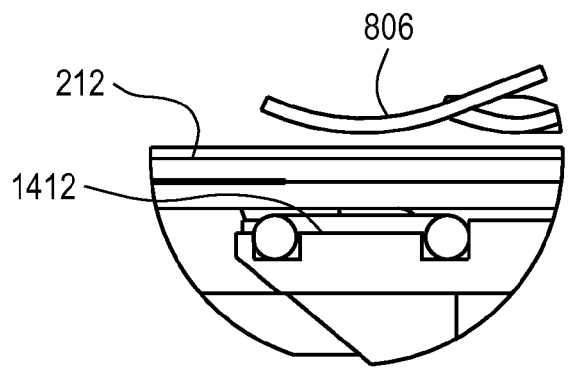
FIG. 15B is a detail view, taken from Detail A of FIG. 15A, of an unclamped slide between a clamp member and a clamp hub in accordance with an embodiment of the invention.

FIG. 15B is a detail view, taken from Detail A of FIG. 15A, of an unclamped slide between a clamp member and a clamp hub in accordance with an embodiment. As shown, in an unclamped configuration, slide 212 may be supported with slide carrier 204 without contacting either finger 806 or clamp seat 1412. Thus, slide 212 may be freely supported within slide carrier 204. Each clamp surface 902 and each clamp seat 1412 may thus provide respective pairs to clamp a respective slide 212 placed therebetween. In an initial freely supported configuration and/or as clamp surfaces 902 and clamp seats 1412 are moved toward each other, e.g., when clamp member 208 and clamp hub 210 move toward each other along longitudinal axis 216, the pairs of clamp surfaces 902 and clamp seats 1412 may be separated by a substantially equivalent distance in the longitudinal direction. Thus, when multiple slides 212 are positioned between clamping pairs, slides 212 may be simultaneously contacted and clamped by respective pairs of clamp surface 902 and clamp seat 1412.

Figure 15C:
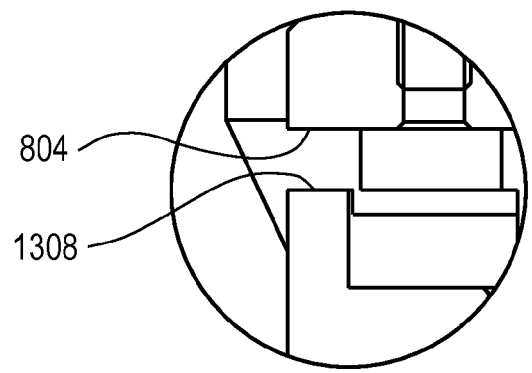
FIG. 15C is a detail view, taken from Detail B of FIG. 15A, of portions of a clamp plate and a central plate hub while a slide is in an unclamped configuration in accordance with an embodiment of the invention.

FIG. 15C is a detail view, taken from Detail B of FIG. 15A, of portions of a clamp plate and a central plate hub while a slide is in an unclamped configuration in accordance with an embodiment. As shown, in an unclamped configuration, a lower surface of clamp plate 804 and an upper surface of clamp hub 1308 may be separated from each other by a clamping gap. For example, the distance between clamp plate 804 and clamp hub 1308 may determine the clamping pressure placed on slide 212, since the closing of the clamping gap is associated with the repeatable clamping of slide 212 between clamp member 806 and clamp seat 1412.

Figure 15D:
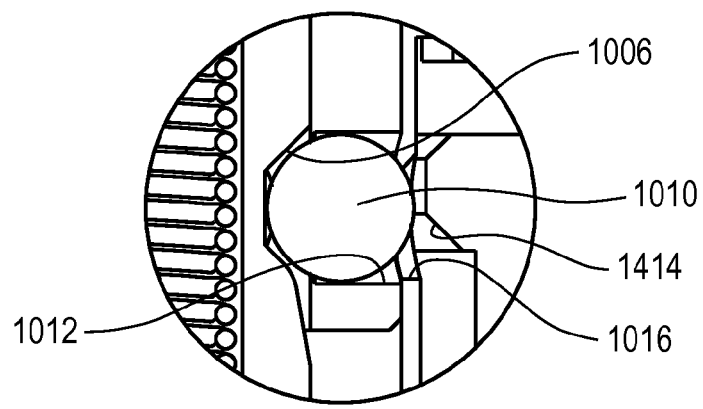
FIG. 15D is a detail view, taken from Detail C of FIG. 15A, of a locking mechanism in an unlocked configuration while a slide is in an unclamped configuration in accordance with an embodiment of the invention.

FIG. 15D is a detail view, taken from Detail C of FIG. 15A, of a locking mechanism in an unlocked configuration while a slide is in an unclamped configuration in accordance with an embodiment. As shown, lock ball 1010 may be recessed within shaft groove 1006 in the unlocked configuration, such that lock ball 1010 does not protrude outward through spindle cap slot 1016. Therefore, lock ball 1010 does not exert a retention force on lock chamfer 1414. As a result, clamp member 208 and clamp hub 210 may remain free to move relative to each other in the unclamped configuration.

Figure 15E:
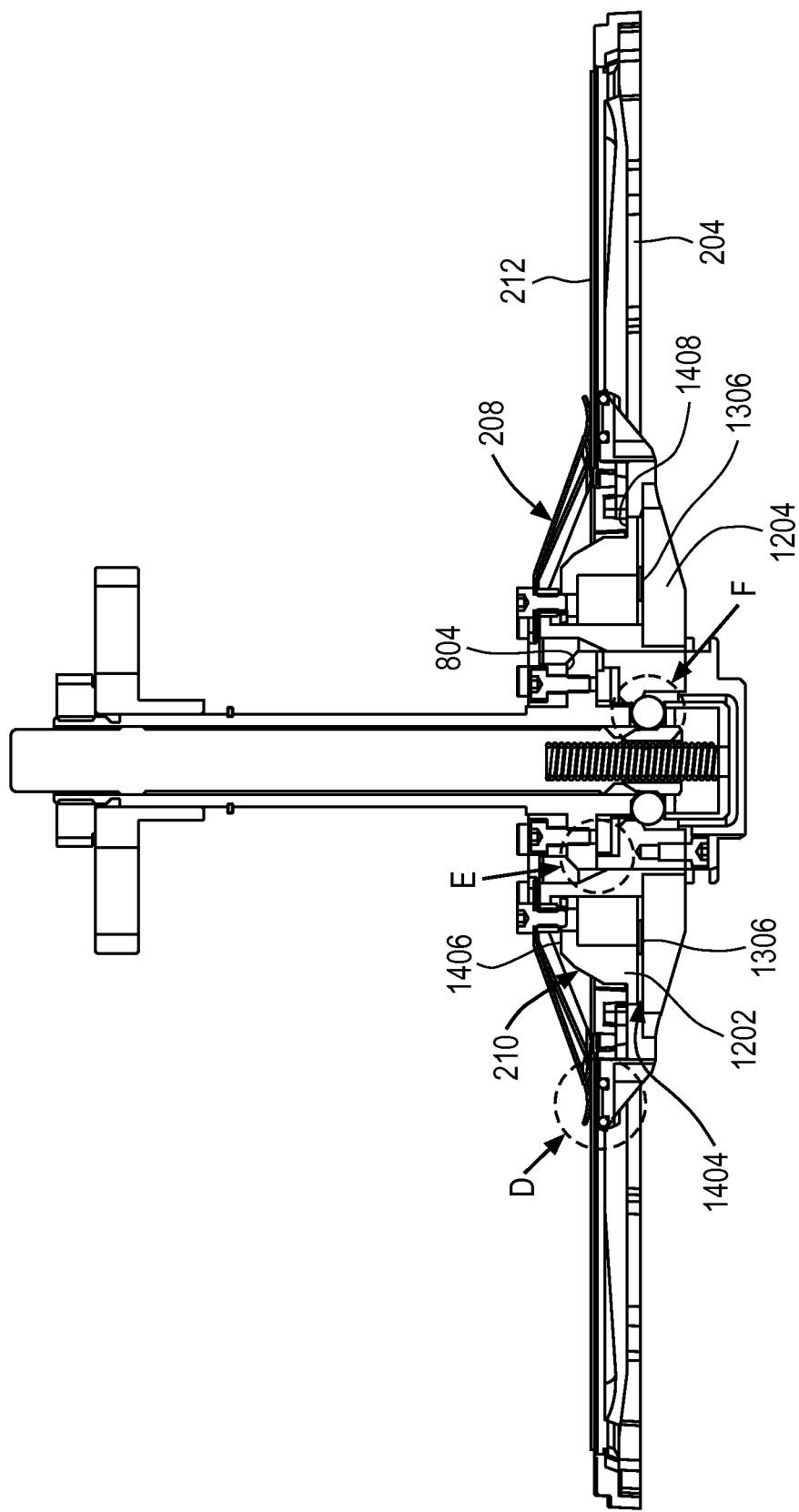
FIG. 15E is a cross-section view of a slide carrier resting on a clamp hub with a slide clamped between the clamp hub and a clamp member in accordance with an embodiment of the invention.

Referring to FIG. 15E, a cross-section view of a slide carrier resting on a clamp hub with a slide clamped between the clamp hub and a clamp member is shown in accordance with an embodiment. In a second configuration, additional loading may be placed on spring 1306, causing slide carrier receiver 1202 to deflect further toward slide seating plate 1204. More particularly, as clamp hub 210 supporting slide carrier 204 is raised toward clamp member 208 by hub drive 214, a lower surface of a portion of clamp plate 804 may engage an upper surface of a portion of central plate hub 1308. Simultaneously, a portion of clamp plate 804 may press downward on receiver tooth 1406 of slide carrier receiver 1202. This additional pressure on slide carrier receiver 1202, in addition to the weight of slide carrier 204 resting on receiver support 1408, may be sufficient to compress spring 1306 and reduce bias gap 1404. As bias gap 1404 reduces, slide carrier 204 may be supported on receiver support 1408 separately from slides 212. More particularly, as slide carrier 204 drops below slides 212 on the moving receiver support 1408, clamp seat 1412 and clamp surface 902 may grip slides 212 firmly and maintain slides 212 in a lifted position, resulting in a physical separation of slides 212 and slide carrier 204.

Figure 15F:
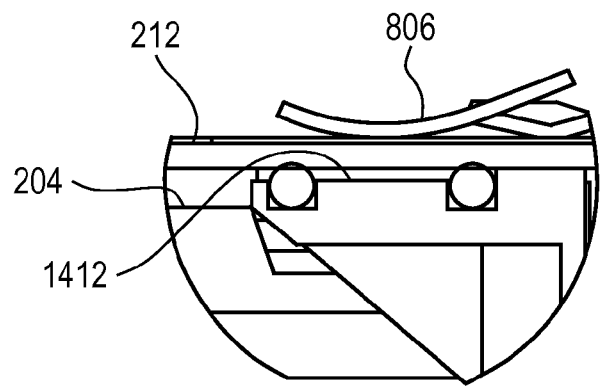
FIG. 15F is a detail view, taken from Detail D of FIG. 15B, of a clamped slide between a clamp member and a clamp hub in accordance with an embodiment of the invention.

FIG. 15F is a detail view, taken from Detail D of FIG. 15B, of a clamped slide between a clamp member and a clamp hub in accordance with an embodiment. As shown, in the clamped configuration, clamping member 806 and clamp seat 1412 may exert a clamping force on slides 212. For example, clamp member 806 may press downward on an upper surface of slide 212 while an elastomeric O-ring associated with clamp seat 1412 presses upward on a lower surface of slide 212. In the clamped configuration, slides 212 may be held above slide carrier 204.

Figure 15G:
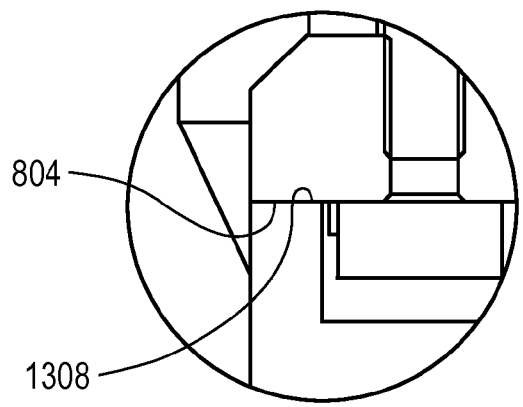
FIG. 15G is a detail view, taken from Detail E of FIG. 15B, of portions of a clamp plate and a central plate hub while a slide is in a clamped configuration in accordance with an embodiment of the invention.

FIG. 15G is a detail view, taken from Detail E of FIG. 15B, of portions of a clamp plate and a central plate hub while a slide is in a clamped configuration in accordance with an embodiment. As shown, in the clamped configuration a lower surface of a portion of clamp plate 804 may engage an upper surface of a portion of central plate hub 1308 after moving clamp plate 804 toward central plate hub 1308. Collision of the parts may be used as a repeatable stop to determine a clamping pressure. For example, since clamp plate 804 and central plate hub 1308 make contact, the point of contact serves as a datum at which the clamping distance between finger 806 and clamp seat 1412 is the same from viewing session to viewing session. Thus, slide 212 is reliably gripped within a known range of pressures between finger 806 and clamp seat 1412.

Figure 15H:
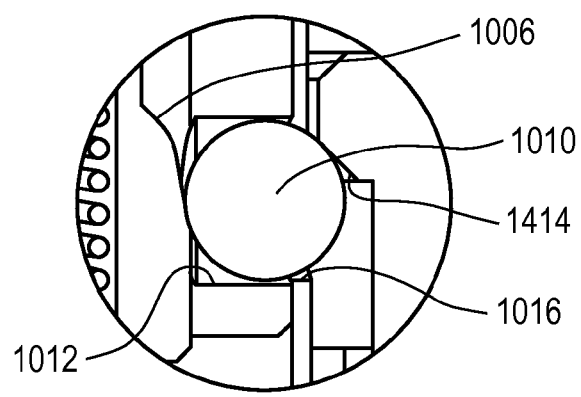
FIG. 15H is a detail view, taken from Detail F of FIG. 15B, of a locking mechanism in a locked configuration while a slide is in a clamped configuration in accordance with an embodiment of the invention.

FIG. 15H is a detail view, taken from Detail F of FIG. 15B, of a locking mechanism in a locked configuration while a slide is in a clamped configuration in accordance with an embodiment. As shown, movement of shaft 1004 in a longitudinal direction may cause shaft groove 1006 to misalign with lock ball 1010 and lock ball 1010 may thus be forced out through spindle cap slot 1016. Furthermore, as lock ball 1010 protrudes through spindle cap slot 1016, it may engage lock chamfer 1414, coupling clamp member 208 with clamp hub 210. In the coupled configuration, slides 212 may be gripped between clamp member 208 and clamp hub 210.

Figure 16:
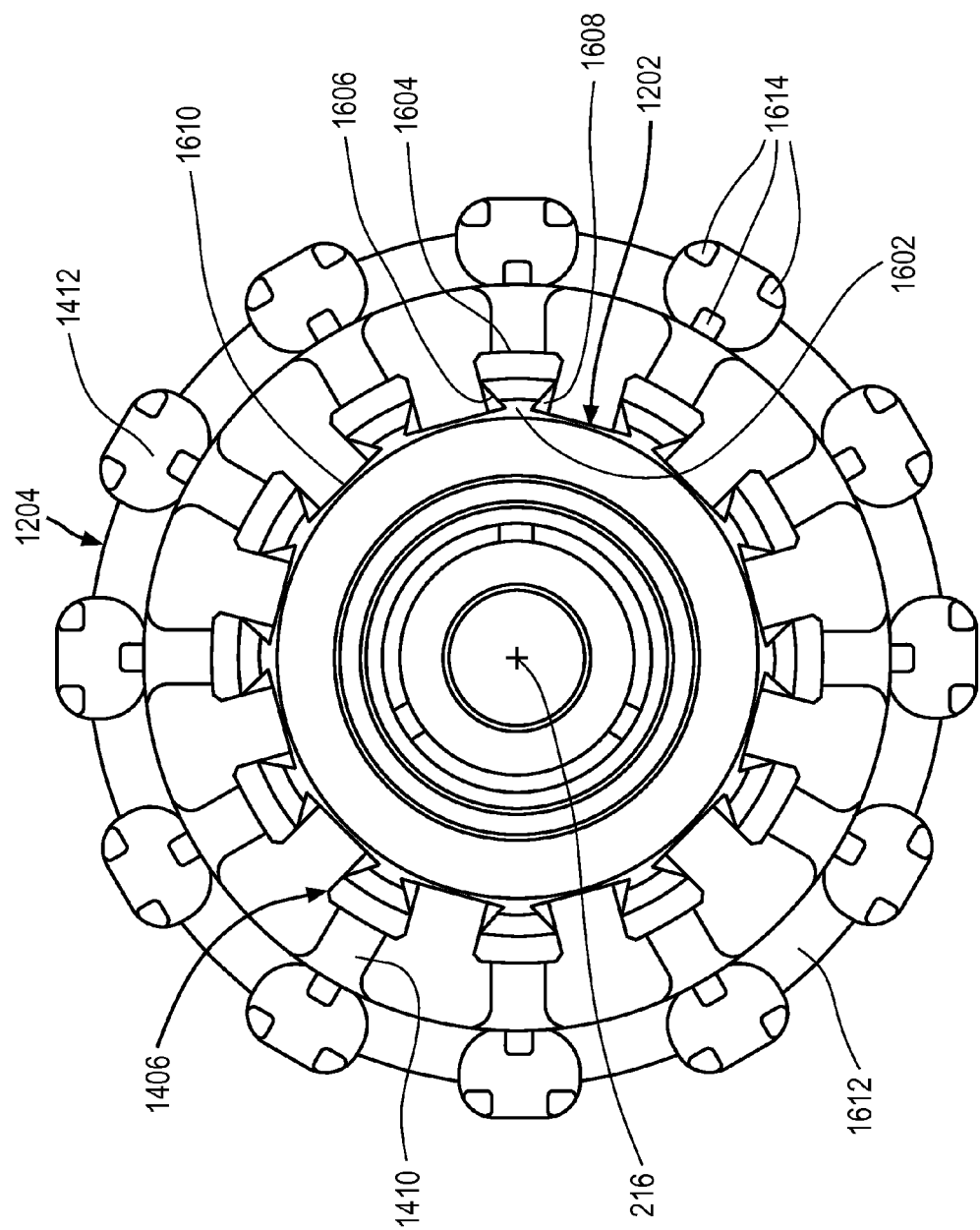
FIG. 16 is a top view of a clamp hub of a microscope in accordance with an embodiment of the invention.

Referring to FIG. 16, a top view of a clamp hub of a microscope is shown in accordance with an embodiment. Slide carrier receiver 1202 and slide seating plate 1204 may be radially aligned along longitudinal axis 216. Furthermore, each receiver tooth 1406 of slide carrier receiver 1202 may be rotationally aligned with a corresponding clamp seat 1412 on slide seating plate 1204. Accordingly, as receiver tooth 1406 meshes with carrier tooth 312, a slide 212 held in slide receptacle 404 will become rotationally aligned with clamp seat 1412. In other words, slide receptacles 404 may be offset between carrier teeth 312 such that they align with clamp seats 1412 when receiver teeth 1406 and carrier teeth 312 mesh.

In an embodiment, each receiver tooth 1406 is configured to facilitate meshing with carrier teeth 312 even when clamp hub 210 and slide carrier 204 are brought together, even when clamp hub 210 and slide carrier 204 are initially rotationally misaligned. For example, receiver tooth 1406 may be narrower at root 1602 than at an addendum 1604. That is, receiver tooth 1406 may taper outward along flank 1608 such that it has tapered edge 1606. Thus, as clamp hub 210 advances toward slide carrier 204, the narrow root 1602 of receiver tooth 1406 will mesh between carrier teeth 312. If, in an embodiment, carrier teeth 312 and receiver teeth 1406 are slightly misaligned in a rotational direction, carrier teeth will slide along tapered edge 1606 as clamp hub 210 is advanced further until an outer edge of carrier teeth 312 becomes centered between receiver teeth flanks 1608 adjacent bottom land 1610.

In an embodiment, clamp seats 1412 on slide seating plate 1204 are circumferentially arranged along wheel 1612 about longitudinal axis 216. One or more clamp seat 1412 may furthermore be rotationally aligned with spokes 1410 of slide seating plate 1204. The circumferential arrangement of clamp seats 1412 may correspond to the circumferential arrangement of clamp surfaces 902 on clamp member 208. Thus, when clamp member 208 and clamp hub 210 are radially aligned, clamp surfaces 902 and clamp seats 1412 may be rotated into longitudinal alignment with each other to match gripping surfaces. That is, clamp surfaces 902 and clamp seats 1412 may become aligned such that they may be brought toward each other to clamp an object placed therebetween, e.g., a slide 212.

Each clamp seat 1412 may also include one or more boss 1614. Boss 1614 may be a protruding structure, such as a flat-faced nub or a pointed nib that protrudes longitudinally toward a corresponding clamp surface 902. Optionally, bosses 1614 are arranged along an outer edge of clamp seat 1412 such that the center of pressure provided by clamp surface 902 near a center of the boss 1614 arrangement. Furthermore, the combined surface area of bosses 1614 on clamp seat 1412 may be less than a surface area of clamp seat 1412. In an embodiment, bosses 1614 and clamp seat 1412 may be formed from a material that is harder than clamp nub 808. For example, whereas clamp nub 808 may be formed from an elastomer, in an embodiment, clamp seat 1412 and bosses 1614 are formed from a metal such as steel or anodized aluminum.

Figure 17:
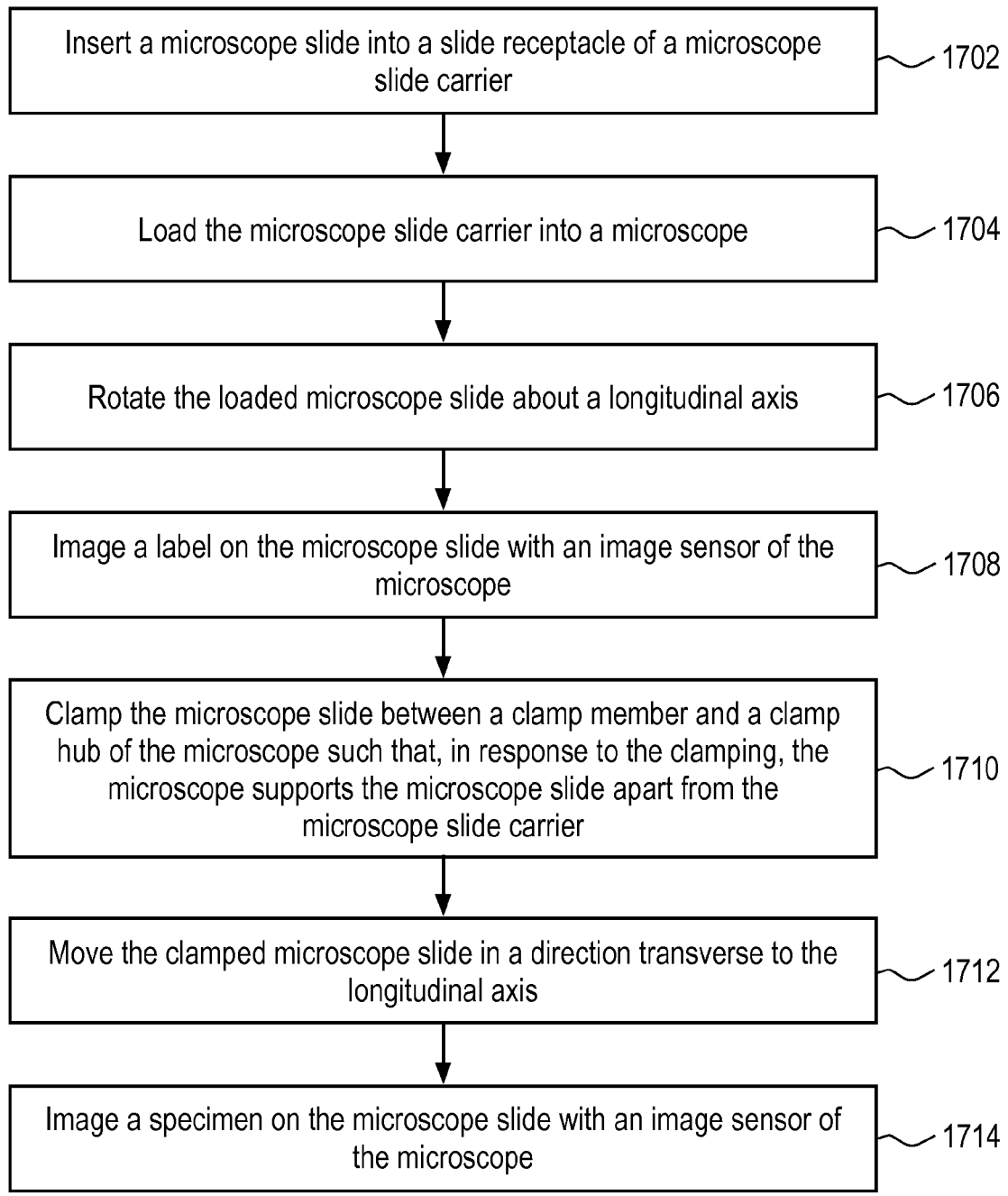
FIG. 17 is a flowchart of a method of imaging a microscope slide in accordance with an embodiment of the invention.

Referring to FIG. 17, a flowchart of a method of imaging a microscope slide is shown in accordance with an embodiment. Operations provided in the flowchart are described below in combination with FIGS. 18A-18D, which provide perspective views of microscope 104 configurations corresponding to the various method operations. At operation 1702, a microscope slide 212 having a specimen for viewing may be inserted into slide receptacle 404 of slide carrier 204. In an embodiment, the slide 212 is loosely supported in slide carrier 204. For example, slide 212 may rest on carrier support 410 within outer profile 406 of slide receptacle 404 such that gap 416 surrounds the slide 212. Loading of a slide 212 into the slide carrier 204 may be performed by a pathologist or a lab technician. The user may load a single slide 212, or multiple slides 212 may be loaded into slide carrier 204 by loading each slide 212 into a respective slide receptacle 404. Generally, slides 212 are mixed after preprocessing of the slides 212. That is, slides 212 from several patients may be intermixed and subjected to the same staining process. Subsequently, a technician may sort the slides 212 according to an individual patient. However, in an embodiment, patient and/or slide information is included in data printed or contained within label area 412 of slide 212. Thus, the need to sort meticulously may be less crucial using slide carrier 204 given that microscope 104 will be able to automatically identify and categorize imaged information according to information provided in the label area 412. As described above, this identification may be performed using visual techniques, e.g., optical character recognition, or with RFID transmissions, barcode scanning, or other data communication methods. In any case, slides 212 can be loaded in any order without negatively impacting downstream processes, unlike current methods that require visual sorting and initial organization of slides.

Figure 18A:
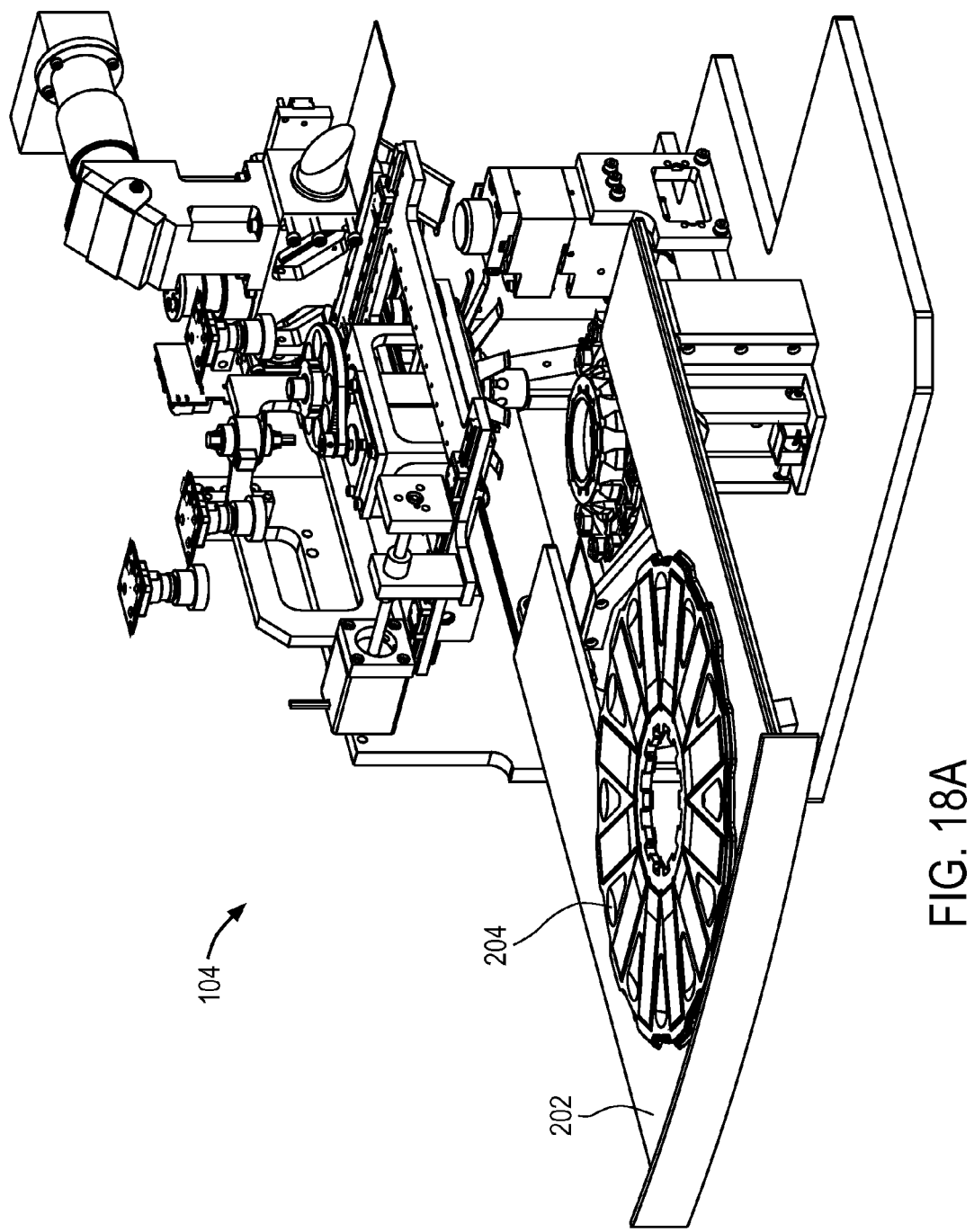
FIGS. 18A-18D are perspective views of various operations for imaging a microscope slide in accordance with an embodiment of the invention.

Referring to FIG. 18A, a perspective view of a slide carrier loaded into an extended shelf of a microscope is shown in accordance with an embodiment. At operation 1704, slide carrier 204 is loaded onto shelf 202 of microscope 104. Outer profile 406 of slide carrier 204 may engage a matching recess in shelf 202 to ensure that slide carrier 204 remains rotationally constrained as it is moved toward slide clamping assembly 700 of microscope 104. Microscope 104 may include an enclosure having a door or other opening that shelf 202 slides within. Such an enclosure may include any contour that encompasses the microscope 104 components. For example, the enclosure may be formed as a box-like enclosure with flat outer surfaces and walls, or portions of the surfaces and walls may be curved to provide an aesthetic form factor.

Figure 18B:
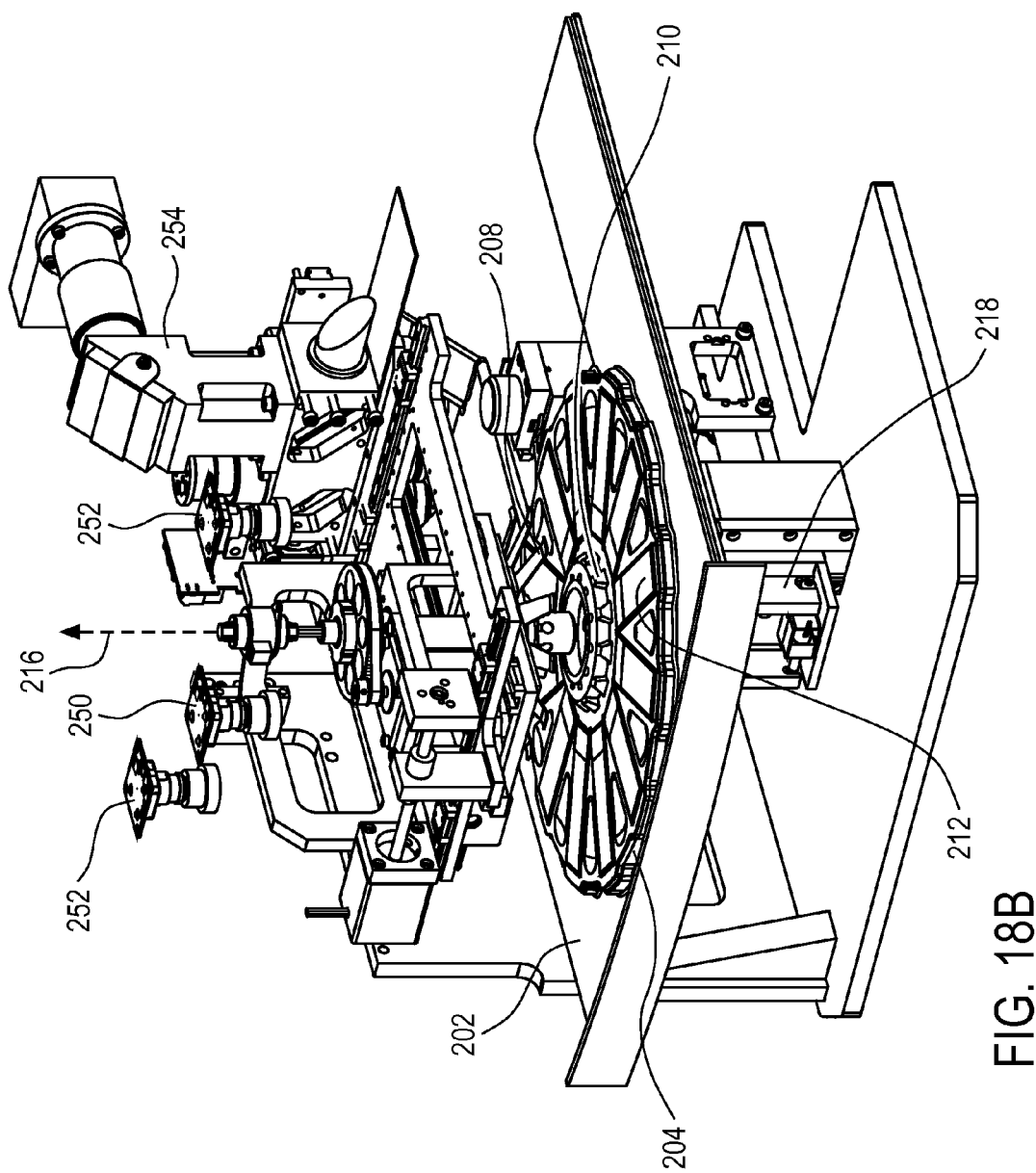

Referring to FIG. 18B, a perspective view of a label camera of a microscope imaging a label area of a slide is shown in accordance with an embodiment. Slide carrier 204 may be advanced along x-axis 206 until clamp hub 210 is radially aligned with central opening 316 of slide carrier 204. Clamp hub 210 may then be raised by z-stage 218 until carrier teeth 312 and receiver teeth 1406 mesh. As described above, the meshing may occur passively, as the tapered form of receiver teeth 1406 correct any misalignment between slide carrier 204 and clamp hub 210. Alternatively, hub drive 214 may rotate clamp hub 210 as it is raised to engage carrier teeth 312 and receiver teeth 1406 based on feedback provided by a sensor in the system, such as a proximity sensor or a rotary encoder. Z-stage 218 may continue to drive clamp hub 210 along longitudinal axis 216 until slide carrier 204 is lifted above shelf 202. For example, slide carrier 204 may rest above shelf 202 on receiver support 1408 with spring 1306 pressing slide carrier receiver 1202 against bushing lip 1402. In this configuration, slide carrier 204 may be rotated freely about longitudinal axis 216 without contacting shelf 202 or other components of microscope 104, e.g., clamp member 208.

At operation 1706, slide carrier 204 and any microscope slides 212 held loosely in slide receptacles 404 of slide carrier 204 may be rotated about longitudinal axis 216. For example, hub drive 214 may rotate clamp hub 210 about longitudinal axis 216 while slide carrier receiver teeth 1406 engage slide carrier teeth 312. Thus, rotational motion may be imparted through the system to slide carrier 204.

At operation 1708, label area 412 on slide 212 may be imaged by label camera 250. Simultaneously or consecutively, slides 212 may also be viewed by overview camera 252 to obtain an overview image of each slide 212. In an embodiment, label camera 250 and/or overview camera 252 may be fixed to a frame of microscope 104 at an oblique angle relative to upper surface 304 of slide 212. For example, label camera 250 may be angled to view label area 412 that is directly underneath stages of clamp member motion sub-system 120. Overview camera 252 may be located to view slide 212 in a longitudinal direction. In an embodiment, image sensor 108 of label camera 250 and/or image sensor 108 of overview camera 252 captures an unmagnified image of the entire label area 412. However, in an alternative embodiment, label camera 250 and/or overview camera 252 may capture several unmagnified images of portions of slide 212 that may subsequently be combined into a single image of label area 412 and/or specimen area 414 for viewing on a display screen. For example, label area 412 may be imaged as a portion by label camera 250, overview camera 252 may image three adjacent areas of specimen area 414, and then all four imaged areas may be pieced together into an overview image using image processing techniques. Slide carrier 204 may be indexed from slide to slide by rotation of hub drive 214 until all areas of interest have been imaged by label camera 250 and overview camera 252. Throughout the imaging process, movement of slides 212 may be accomplished independently from label camera 250 and overview camera 252, which may remain stationary and fixed to a frame of microscope 104, thereby providing stability of the vision system. Given the speed of indexing from slide to slide using a rotational motion system, in an embodiment, even with twelve or more slides held in slide carrier 204, label and overview images for all of the slides are captured within about thirty seconds.

Figure 18C:
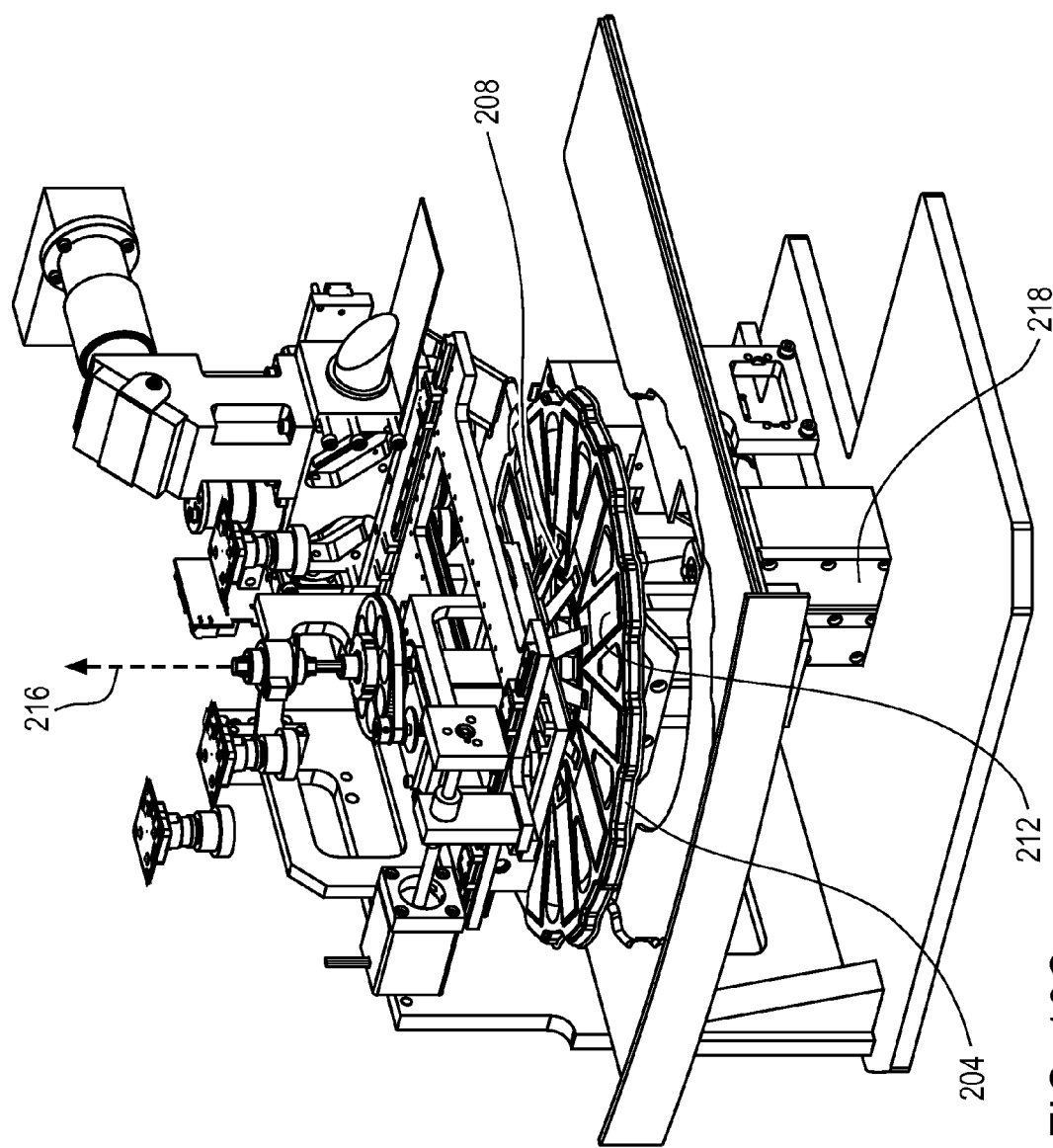

Referring to FIG. 18C, a perspective view of a plurality of slides being gripped between a clamp member and a clamp hub while the slides become physically separated from a slide carrier is shown in accordance with an embodiment. At operation 1710, clamp hub 210 may be raised along longitudinal axis 216 by z-stage 218 until one or more of slides 212 held loosely in slide carrier 204 become gripped between clamp member 208 and clamp hub 210. More particularly, in an embodiment, clamp nub 808 on finger 806 of clamp member 208 contacts an upper surface of label area 412 and boss 1614 on slide seat 1412 of clamp hub 210 contacts a lower surface of label area 412 such that slide 212 becomes fixedly clamped between clamp member 208 and clamp hub 210. In an embodiment, gripping may be effected by actuation of spindle 230 to lock clamp hub 210 to clamp member 208 as described above. In an embodiment, a plurality of slides may be gripped simultaneously.

It will be appreciated that gripping of slides 212 may be achieved in numerous manners other than clamping. More specifically, although the terms "clamp", "clamping", etc. are used frequently throughout this disclosure, other means of gripping slide 212 to remove slide 212 from slide receptacle 404 and to support and move slide 212 during imaging may be used. For example, rather than support slide 212 from both sides, e.g., by clamping slide 212 between clamp surface 902 and clamp seat 1412, slides 212 may be supported on a single side. In an embodiment, this may be achieved by using a vacuum port at clamp surface 902 to create a suction between slides 212 and clamp surfaces 902 of clamp member 208. Alternatively, gripping mechanisms such as nut-and-groove type holding mechanism may be employed to grip slides 212 without clamping slides 212 between two surfaces. As another example, clamp surfaces 902 may include a protruding feature, such as a peg, that engages a recess feature, such as a hole, in a surface of slide 212. The protruding feature and recess feature may form a friction fit. Accordingly, clamp surface 902 may lift slide 212 from slide carrier 204 by gripping slide 212 with only a single point of contact. Numerous other manners of gripping or otherwise securing or applying traction to an object are known in the art and considered to be within the scope of this disclosure. Thus, slides 212 may be gripped in manners other than clamping.

In response to the clamping, slides 212 become fixedly supported by slide clamping assembly 700. Simultaneously with the clamping, slides 212 may be lifted away from carrier support 410 of slide receptacle 404. Thus, rather than being loosely supported by slide carrier 204, slides 212 may become fixedly supported by slide clamping assembly 700. Accordingly, in an embodiment, microscope slides 212 are physically separated and spaced apart from slide carrier 204 after the clamping. The slides 212 may be arranged in a circumferential pattern about longitudinal axis 216 when supported fixedly supported by slide clamping assembly 700. In an embodiment, clamping force is passively managed based on the repeatability of actuation of locking mechanism 1002. That is, given that lock ball 1010 consistently grips lock chamfer 1414, a relative distance between clamp seat 1412 and clamp surface 902 when locking mechanism 1002 is actuated remains consistently the same. Thus, since the distance between clamp surface 902 and clamp seat 1412 remains the same, so does the clamping pressure on different slides 212, assuming the slides have equal thicknesses. In an embodiment, clamping pressure may be monitored and/or controlled actively. For example, pressure sensors may be integrated within slide clamping assembly 700 to detect force applied to slides 212 between clamp nub 808 and clamp seat 1412. The detected pressure data may be provided as feedback to a control system that actuates motors or actuators to control clamping force.

By virtue of their separation from slide carrier 204, microscope slides 212 may become more closely synchronized with movement of slide clamping assembly 700. For example, given that slides 212 are fixed between clamp member 208 and clamp hub 210, if clamp member 208 and clamp hub 210 are rotated about longitudinal axis 216 by spindle 230, it may be expected that slides 212 will rotate about longitudinal axis 216 by the same amount. By contrast, when slides 212 are loosely supported in slide receptacles 404, movement of slide carrier 204 may not directly correlate in magnitude with movement of slides 212, since slides 212 may be able to slip and rattle within slide receptacles 404 due to gap 416.

Figure 18D:
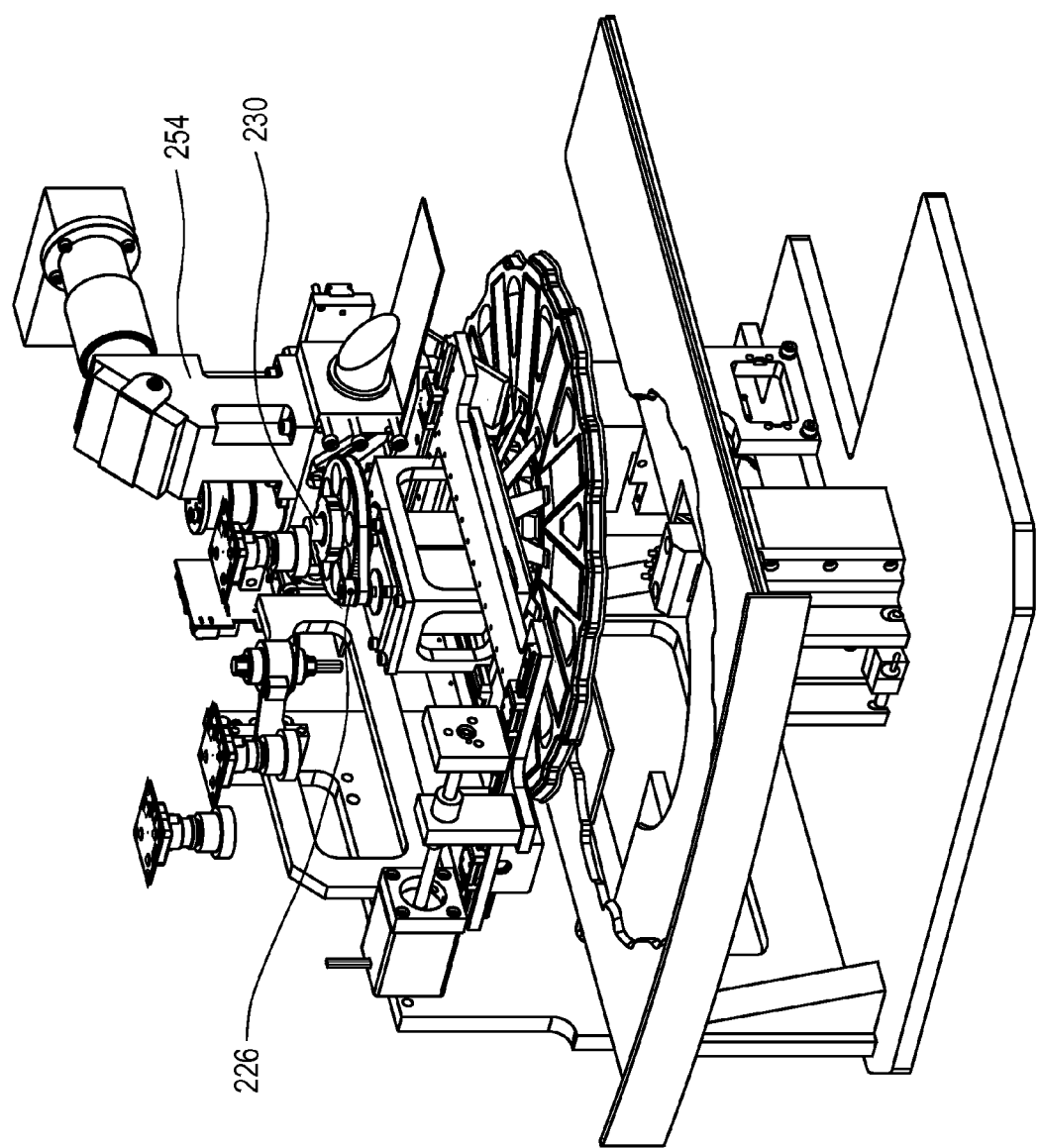

Referring to FIG. 18D, a perspective view of a slide carrier being moved in a transverse plane relative to a specimen camera is shown in accordance with an embodiment. In an embodiment, specimen camera 254 is supported on a frame of microscope 104 and directed in a longitudinal direction. Thus, at operation 1712, in order to view a region of interest of specimen area 414, each slide 212 may be rotated into radial alignment with the field of view of specimen camera 254 in a transverse plane. In an embodiment, this rotational movement of slides 212 occurs after clamping slides 212 and retracting hub drive 214 with z-stage 218. More particularly, slides 212 may be radially aligned with specimen camera 254 using clamp member drive 226 after locking clamp hub 210 with clamp member 208. Movement of slides 212 in this manner may be accomplished with specimen camera 254 fixed to a frame of microscope 104, thereby providing stability of the vision system.

Furthermore, once slide 212 is radially aligned with specimen camera 254, slide 212 may be moved in a transverse plane by movement of spindle 230 effected by x-stage 220 and/or y-stage 222. Movement of spindle 230 in this manner causes slides 212 to be moved in a transverse plane, i.e., perpendicular to longitudinal axis 216. Therefore, slide 212 may be moved within the field of view of specimen camera 254 such that image sensor 108 of specimen camera 254 may capture images of specimen area 414 using the appropriate magnification. For example, a first position on a first slide 212 may be imaged by specimen camera 254.

Imaging of the first position may include capturing and displaying video of the first position, as well as capturing and displaying still images of the first position. In an embodiment, still images may be a single frame of video selected manually or automatically from the video.

Video of the first position on the first slide 212 may include numerous video characteristics. For example, a number of frames per second, aspect ratio, color space, video quality, etc. may all be independently adjustable manually or automatically. As an example, video setting may be adjusted to provide for the capture and display of video at a video rate of at least about fifteen images per second. Video or image settings of specimen camera 254 may also include optical characteristics that may also be adjusted manually or automatically. For example, autofocus may be used to focus on the first position in the region of interest within specimen area 414. During the autofocus procedure, relative motion between slides 212 and objective lenses of specimen camera 254 may be required in a longitudinal direction. This relative movement may be effected by moving spindle 230 with a z-direction motor (not shown) or it may be effected by moving the objective lenses of specimen camera 254 while maintaining slides 212 in the same z-direction position. Given the speed of indexing from slide to slide using a rotational motion system combined with a transverse motion system, in an embodiment, movement from a focused region of interest on a first slide 212 to a focused region of interest on a second slide 212 may be accomplished in less than about two seconds.

At operation 1714, images of specimen regions of interest on slide 212 may be sensed by image sensor 108 of specimen camera 254. The sensed image may also be captured and stored as image data. As explained above, images may be magnified optically using objective lenses and/or digitally through image processing prior to capturing. Captured images may be displayed on a display screen for analysis by a viewer, such as a pathologist. Captured images may be presented in sequence as a video, or a single image may be presented as a still image of an imaged position on slide 212. Slide carrier 204 may be indexed from slide to slide through rotation of spindle 230 by clamp member drive 226 until all specimen areas 414 of interest have been imaged by specimen camera 254. For example, a plurality of fixedly supported slides 212 may be rotated about the longitudinal axis 216 until a second position on a second slide 212 is within the field of view of specimen camera 254. Accordingly, video and/or still images of the second position may be captured by specimen camera 254, and the captured images may be stored in memory and/or displayed on a display device for immediate or later presentation to a viewer.

In an embodiment, the fixed orientation between slides 212 and slide clamping assembly 700 allows for slides 212 to be moved out of view and then returned into view while maintaining the same defined field of view. For example, an image of a region of interest, such as the first position described above, may be captured on a first slide 212 and stored in computer 102 memory and/or displayed on computer 102 display screen. Locations within the first position in the region of interest may be associated with a kinematic reference frame as defined by the various motion sub-systems 114. For example, motion data associated with stepper motors and/or encoders of motion sub-systems 114 may be stored in computer 102 along with images. Accordingly, attention may then be directed to a second slide 212 in a live viewing mode while the captured image of the first slide 212 remains displayed in a display screen region.

Kinematic reference frame information may include not only rotational and transverse locations positions on slides, but may also include information related to the distance between specimen camera 254 and slides 212, including focal length information related to the camera. Thus, after imaging a first position on a first slide 212 and then moving the first slide 212 out of the field of view of specimen camera 254, microscopy system 100 may be used to quickly return the first slide 212 into the field of view and to adjust the position of the first slide 212 or the specimen camera 254 optical characteristics to quickly bring the first position back into focus.

As discussed above, the second position on the second slide 212 may be imaged by specimen camera 254 and video or still images of the second position may be stored in computer 102 memory and/or displayed on computer 102 display screen. Video and/or still images related to the second position may be simultaneously displayed on computer 102 display screen with the video and/or still images related to the first position, which were previously imaged. Thus, a display screen may provide to a viewer a partitioned interface that includes a portion of display showing the first position and a portion of display showing the second position. Additional positions on the first slide 212, the second slide 212, or other slides of the plurality of slides may be imaged and presented to the viewer simultaneously.

While the images related to different positions on one or more slides 212 are being presented to the viewer, if the pathologist wishes to again view the first position in the region of interest on the first slide 212, the first slide 212 may be automatically rotated back into the field of view of the specimen area 414 based on the stored motion data. In an embodiment, the pathologist may make a selection of the first position through a user interface displayed on the display device of computer 102. Other methods of selecting the first position as a current position of interest may also be used. In response to the selection, imaging sub-system 106 and/or motion sub-systems 114 may automatically adjust to cause the selected slide 212 to be rotated back into the field of view of specimen camera 254 and to allow for immediate imaging of the selected position on the selected slide.

For example, given that the first slide 212 is fixed to slide clamping assembly 700 and that the movement of slide clamping assembly 700 is precisely defined by, e.g., stepper motors and or encoders of motion sub-systems 114, if the pathologist selects a captured image representing the first slide 212 or otherwise selects the first position on the first slide 212 as a position of interest, the first position in the region of interest of the first slide 212 may be precisely navigated to within the tolerance of the motion sub-systems 114. In an embodiment, this tolerance may be within about 5 to 10 micron in any direction. The ability to transfer back and forth between slides 212 in this manner allows for comparisons and analyses of the slides 212 to be performed quickly and efficiently. In addition to navigating back to the first position, adjustments by imaging sub-system 106 may also be made to optical characteristics of specimen camera 254 to ensure that the first position may be imaged and viewed on the display device of computer 102.

After specimen areas 414 have been imaged, hub drive 214 may be raised again by z-stage 218 until hub drive 214 engages clamp hub 210, e.g., at end cap 1304. After end cap 1304 is supported by hub drive 214, locking mechanism 1002 may be disengaged by actuation of spindle 230 by spindle actuator 228. Thus, clamp hub 210 may be released from clamp member 208. As clamp hub 210 and clamp member 208 become disconnected, slides 212 that are clamped between fingers 806 and clamp seat 1412 may drop into respective slide receptacles 404. Subsequently, clamp hub 210 may be lowered by z-stage 218 until slide carrier 204 rests on shelf 202. Shelf 202 may then extend away from microscope 104 enclosure along x-axis 206 to expose the slide carrier 204 to a user.

Once the slide carrier 204 is exposed, a user such as a pathologist or technician may remove slide carrier 204 containing slides 212 and stack slide carrier 204 with other slide carriers 204. The stacked configuration of slide carriers 204 may provide for compact storage. Thus, stacks of slide carriers 204 may be transported and archived in an organized and efficient manner. Furthermore, given that stacked slide carriers 204 may cover slides 212 held in adjacent slide carriers 204, the stacking configuration of slide carriers 204 may reduce the risk of contamination.

Figure 19:
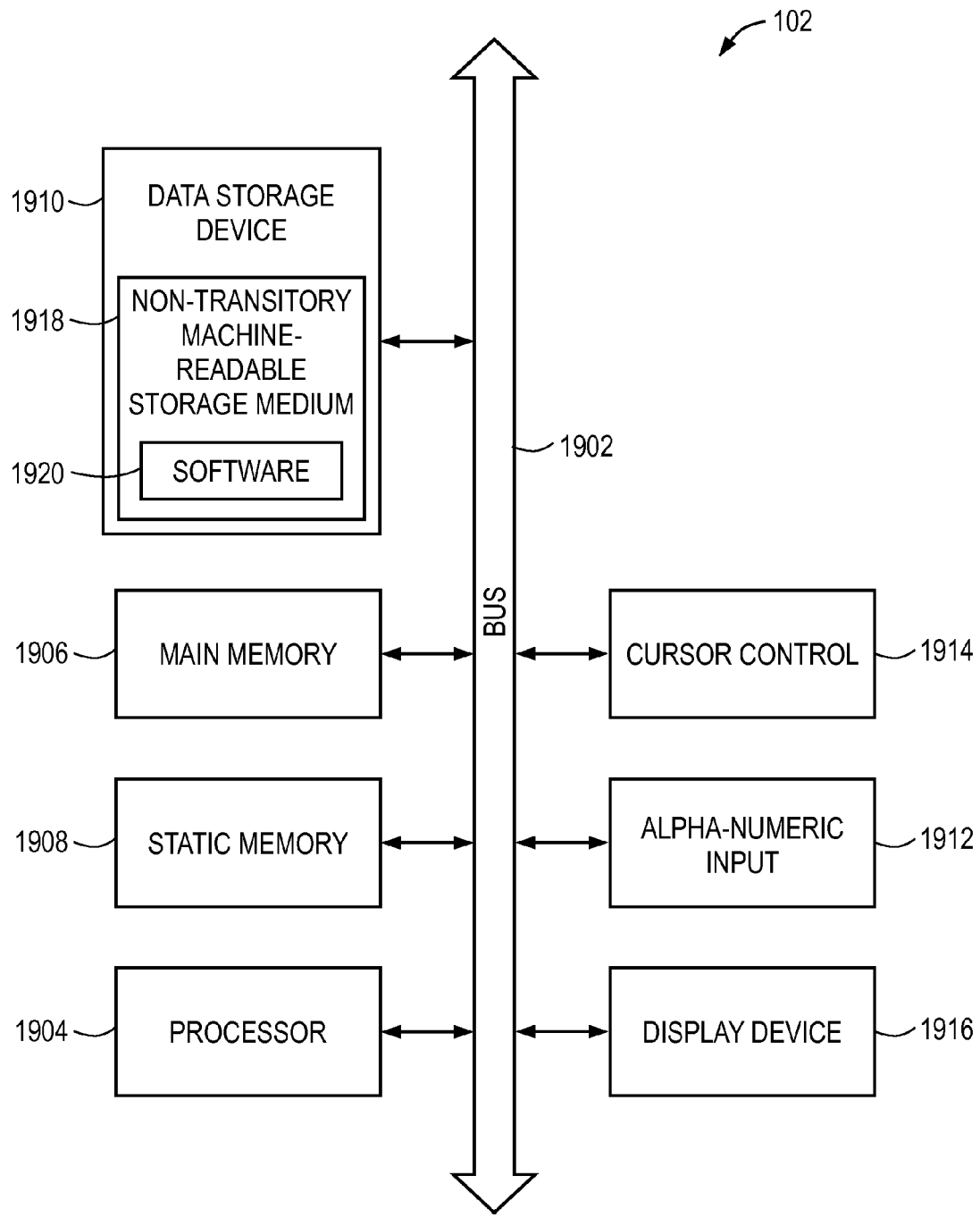
FIG. 19 is a schematic illustration of computer system that may be used in accordance with an embodiment of the invention.

Referring to FIG. 19, a schematic illustration is shown of a computer system that may be used in accordance with an embodiment. Portions of embodiments are comprised of or controlled by non-transitory machine-readable and machine-executable instructions which reside, for example, in machine-usable media of computer 102. Computer 102 is exemplary, and embodiments may operate on or within, or be controlled by a number of different computer systems including general purpose networked computer systems, embedded computer systems, routers, switches, server devices, client devices, various intermediate devices/nodes, stand-alone computer systems, and the like.

Computer 102 of FIG. 19 includes an address/data bus 1902 for communicating information, and central processor unit 1904 connected to bus for processing information, e.g., captured image data, and instructions. Computer 102 also includes data storage features such as computer usable volatile memory 1906, e.g. random access memory (RAM), connected to bus 1902 for storing information and instructions for central processor unit 1904, computer usable non-volatile memory 1908, e.g. read only memory (ROM), connected to bus 1902 for storing static information, e.g., captured image data, and instructions for the central processor unit 1904, and data storage device 1910 (e.g., a magnetic or optical disk and disk drive) connected to bus 1902 for storing information and instructions. Computer 102 of the present embodiment also includes an optional alphanumeric input device 1912 including alphanumeric and function keys connected to bus for communicating information and command selections to central processor unit 1904. Computer 102 also optionally includes an optional cursor control device 1914 connected to bus 1902 for communicating user input information and command selections to central processor unit 1904. Computer 102 of the present embodiment also includes an optional display device 1916, such as a monitor connected to bus 1902 for displaying, e.g., specimen images.

The data storage device 1910 may include a non-transitory machine-readable storage medium 1918 on which is stored one or more sets of instructions (e.g. software 1920) embodying any one or more of the methodologies or operations described herein. Software 1920 may also reside, completely or at least partially, within the computer usable volatile memory 1906, computer usable non-volatile memory 1908, and/or within central processor unit 1904 during execution thereof by computer 102, the computer usable volatile memory 1906, computer usable non-volatile memory 1908, and/or central processor unit 1904 also constituting non-transitory machine-readable storage media.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A microscope slide carrier comprising:
a carrier body comprising an annular disk defined by an outer wall, wherein the carrier body comprises a perimeter contour with a combination of one or more wall protrusions separated by one or more recesses wherein the combination creates an undulating surface around the perimeter of the carrier body, and having an upper surface perpendicular to a longitudinal axis and a central opening through the carrier body along the longitudinal axis;
a plurality of slide receptacles circumferentially spaced about the longitudinal axis in the upper surface, wherein each slide receptacle includes an outer profile extending partially through the carrier body defined by a recess in the upper surface, an inner profile defined by a hole through the carrier body, and a support within the outer profile between the outer profile and the inner profile creating a shelf, wherein the outer profile is larger than an outer perimeter of a microscope slide and is configured to loosely receive a microscope slide, and wherein the support is configured to support the received microscope slide.

2. The microscope slide carrier of claim 1, wherein the inner profile is radially offset from the central opening and the hole through the carrier body defining the inner profile extends fully through the carrier body within the outer profile.

3. The microscope slide carrier of claim 2, wherein the carrier body comprises a central hub radially inward of the plurality of slide receptacles and an inner wall defining a central opening, the inner wall defined by one or more tooth extending radially from the central hub of the carrier body.

4. The microscope slide carrier of claim 3, wherein one or more tooth extends radially inward from the inner wall.

* * * * *